(12) United States Patent
Biwa et al.

(10) Patent No.: US 7,985,376 B2
(45) Date of Patent: Jul. 26, 2011

(54) MEASURING UNIT AND ROTARY VALVE FOR USE THEREIN

(75) Inventors: Seido Biwa, Kobe (JP); Kazunori Mototsu, Kobe (JP)

(73) Assignee: Sysmex Corporation, Hyogo (JP)

( * ) Notice: Subject to any disclaimer, the term of this patent is extended or adjusted under 35 U.S.C. 154(b) by 1214 days.

(21) Appl. No.: 11/443,065

(22) Filed: May 31, 2006

(65) Prior Publication Data
US 2006/0216213 A1 Sep. 28, 2006

Related U.S. Application Data

(63) Continuation of application No. 10/144,737, filed on May 15, 2002, now abandoned.

(30) Foreign Application Priority Data

May 15, 2001 (JP) .................... 2001-145084
Dec. 27, 2001 (JP) .................... 2001-397726

(51) Int. Cl.
*G01N 15/06* (2006.01)
(52) U.S. Cl. ....... 422/68.1; 422/500; 422/502; 422/503; 422/82.01
(58) Field of Classification Search ............. 422/63–67, 422/99–100, 68.1, 500, 502–503, 82.01; 436/180
See application file for complete search history.

(56) References Cited

U.S. PATENT DOCUMENTS

| | | | |
|---|---|---|---|
| 4,729,876 A | 3/1988 | Hennessy et al. | |
| 5,228,350 A | 7/1993 | Karpf et al. | |
| 5,270,212 A * | 12/1993 | Horiuchi et al. | 436/45 |
| 5,681,529 A | 10/1997 | Taguchi et al. | |
| 5,697,899 A * | 12/1997 | Hillman et al. | 604/28 |
| 6,037,178 A | 3/2000 | Leiner et al. | |

FOREIGN PATENT DOCUMENTS

| | | |
|---|---|---|
| DE | 10057895 A1 | 5/2002 |
| EP | 0107631 A2 | 5/1984 |
| WO | WO-93/17328 A1 | 9/1993 |
| WO | WO-99/01742 A1 | 1/1999 |

* cited by examiner

*Primary Examiner* — Jyoti Nagpaul
(74) *Attorney, Agent, or Firm* — Birch, Stewart, Kolasch & Birch, LLP

(57) ABSTRACT

A measuring unit includes a quantifying section for quantifying a sample in volume, a main channel communicating with the quantifying section, an analyzing section provided in the main channel for analyzing the quantified sample, and a pressure introduction port communicating with the main channel for introducing a pressure into the main channel to transport the sample from the quantifying section to the analyzing section, wherein the analyzing section comprises at least one of an electrical characteristic measuring section for measuring an electrical characteristic of the sample and an optical characteristic measuring section for measuring an optical characteristic of the sample.

23 Claims, 48 Drawing Sheets

MEASURING UNIT AND ROTARY VALVE FOR USE THEREIN

CROSS-REFERENCE TO RELATED

This application is a continuation application of U.S. patent application Ser. No. 10/144,737 filed May 15, 2002, now abandoned, which is related to Japanese Patent Applications Nos. 2001-145084 filed in May 15, 2001 and 2001-397726 filed in Dec. 27, 2001, whose priorities are claimed under 35 USC §119, the disclosures of which are incorporated by reference in their entirety.

BACKGROUND OF THE INVENTION

1. Field of the Invention

The present invention relates to a measuring unit and a valve for use therein. Particularly, the invention relates to a measuring unit for analysis of particles in a liquid sample.

2. Description of the Related Art

The following is prior-art devices related to the present invention.

(1) A biological fluid analyzing device for analyzing biological fluid by measuring optical characteristics of a sample, the device comprising: a sample receiving port and a pump connection port; at least one sample treating chamber, an optical measuring chamber and, optionally a waste liquid reservoir provided between the sample receiving port and the pump connection port; and a fluid pathway connecting the sample treating chamber, the optical measuring chamber and/or the waste liquid reservoir chamber (e.g., U.S. Pat. No. 5,681,529).

(2) A disposable measuring element comprising: a measuring channel with at least one optical or electrochemical sensor located therein; a first port provided at a first end of the measuring channel for connecting the measuring element to an analyzer; and a second port provided at a second end of the measuring channel for connecting the measuring element to a sample taking part, wherein a single common sealing element is provided for the first and second ports, and has first, second and third positions, wherein the first and second ends of the measuring channel are closed when the sealing element is at the first position, wherein the first end of the measuring channel is connected to the first port and the second end of the measuring channel is connected to a collecting tank provided in the measuring element for collecting liquid discharged from the measuring channel when the sealing element is at the second position, wherein the first end of the measuring channel is connected to a buffer tank provided in the measuring element and the second end of the measuring channel is connected to the second port when the sealing element is at the third position (e.g., U.S. Pat. No. 5,228,350).

With the aforesaid arrangements, the measuring unit (the biological fluid analyzing device or the measuring element) contaminated by a sample is discarded after use, so that a user can perform a sample analyzing operation safely and sanitarily.

However, the conventional measuring unit is not designed to accurately quantify a given sample. Therefore, it is difficult to accurately analyze biological fluid samples such as blood and urine, industrial particulate samples such as toner particles, and drink samples such as milk.

A conceivable approach to this problem is to preliminarily quantify the sample to be applied to the measuring unit. However, this approach additionally requires a device for quantifying the sample, which may also be contaminated by the sample.

Further, it is difficult to properly match the measuring unit with an additional sample quantifying and diluting device for accurate analysis of the sample with good reproducibility.

SUMMARY OF THE INVENTION

In view of the foregoing, it is an object of the present invention to provide a measuring unit which has a sample quantifying function to analyze a given sample safely and sanitarily.

In accordance with the present invention, there is provided a measuring unit, which comprises: a quantifying section for quantifying a sample in volume; a main channel communicating with the quantifying section, an analyzing section provided in the main channel for analyzing the quantified sample, and a pressure introduction port communicating with the main channel for introducing a pressure into the main channel to transport the sample from the quantifying section to the analyzing section, wherein the analyzing section comprises at least one of an electrical characteristic measuring section for measuring an electrical characteristic of the sample and an optical characteristic measuring section for measuring an optical characteristic of the sample.

DETAILED DESCRIPTION OF THE INVENTION

Figure 1:
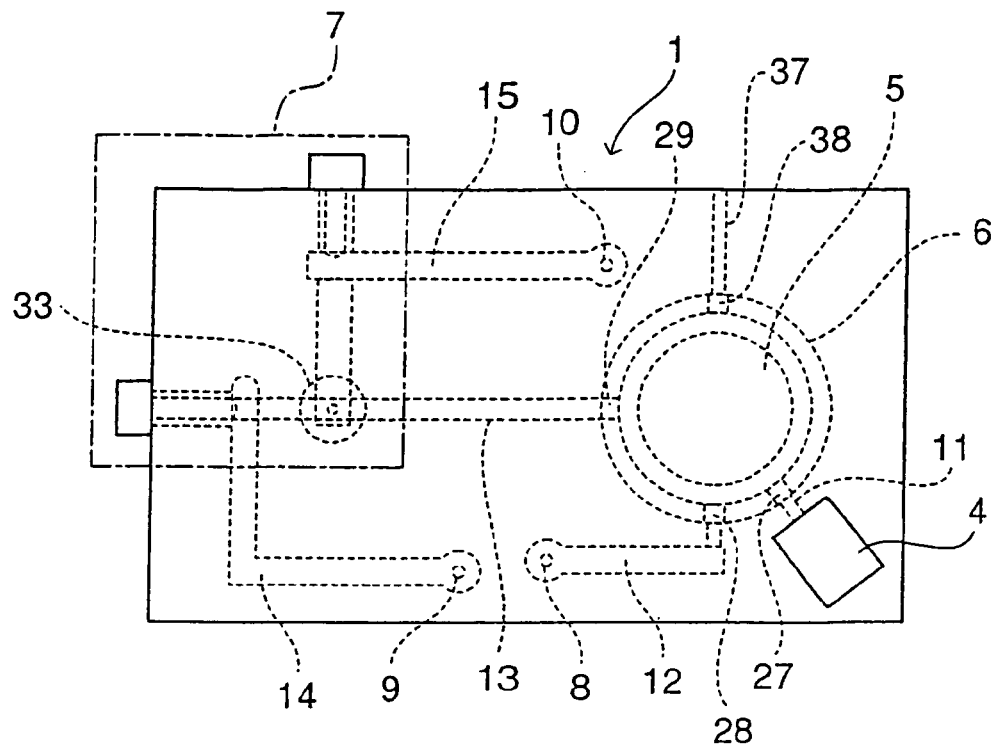
FIG. 1 is a top plan view of a measuring unit according to a first embodiment of the present invention.

The measuring unit according to the present invention comprises: a measuring unit comprising: a quantifying section for quantifying a sample in volume; a main channel communicating with the quantifying section, an analyzing section provided in the main channel for analyzing the quantified sample, and a pressure introduction port communicating with the main channel for introducing a pressure into the main channel to transport the sample from the quantifying section to the analyzing section, wherein the analyzing section comprises at least one of an electrical characteristic measuring section for measuring an electrical characteristic of the sample and an optical characteristic measuring section for measuring an optical characteristic of the sample.

The analyzing section may comprise either or both of the electrical characteristic measuring section and the optical characteristic measuring section. The electrical characteristic measuring section is typically adapted to measure the size and number of particles in the sample, while the optical characteristic measuring section is typically adapted to measure the absorbance of the sample. More specifically, the electrical characteristic measuring section measures the size and number of red blood cells, white blood cells, platelets, toner particles, or the like. The optical characteristic measuring section determines the amount of hemoglobin, a blood coagulation period, the activity level of an enzyme such as ALP or a peroxidase, the amount of bilirubin, CRP, or the like.

The quantifying section may comprise a diluting section for diluting the sample to be analyzed with a predetermined volume of diluent. The measuring unit may further comprise a sample receiving section for receiving the sample to be quantified, the sample receiving section communicating with the quantifying section. The sample receiving section is configured so as to receive a capillary blood sampler inserted therein.

In the measuring unit, the quantifying section may include a rotary valve, which includes an outer cylinder having an open bottom and a cylindrical inner circumferential surface, and an inner cylinder having a closed bottom and a recess provided in an outer circumferential surface thereof for quantifying the sample, the inner cylinder being fitted in the outer cylinder and rotatable about an axis thereof in sliding contact with the inner circumferential surface of the outer cylinder, the outer cylinder and the inner cylinder defining a diluent container for containing the diluent.

The rotary valve may further comprise a first channel for introducing the sample into the recess, and a second channel for allowing the recess to communicate with the diluent container, wherein the inner cylinder is rotated to open and close the first channel and the second channel.

The inner cylinder may be rotated to open the first channel for introducing the sample into the recess, to close the first channel for quantifying the sample, and to open the second channel for transporting the quantified sample into the diluent container for dilution of the sample.

The electrical characteristic measuring section may comprise a separation plate having a small through-hole and provided in the main channel to obstruct the main channel, and two electrodes exposed to the main channel on opposite sides of the separation plate.

Usable as the separation plate is an electrically insulative round sheet having a thickness of 50 μm to 500 μm and an outer diameter of 0.5 mm to 10 mm and formed with a minute through-hole having a diameter of 50 μm to 300 μm. The diameter of the minute through-hole is preferably determined depending on the size of the particles to be measured. Preferred examples of a material for the sheet include heat-resistant plastics such as polyimides, but not limited thereto. Other exemplary materials for the sheet include ruby and sapphire. With the use of a heat-resistant material, the formation of the minute through-hole can easily be achieved by a laser machining process such as an excimer laser abrasion process. The separation plate is cut out of a sheet material by a $CO_2$ laser process or a stamping process, which is preferred for cost reduction.

The optical characteristic measuring section is preferably located in a portion of the main channel, which is pervious to light and configured so as to be interposed between a light source and a light receiving device.

The measuring unit may comprise an upper plate and a lower plate stacked on the upper plate, and the quantifying section, the main channel and the analyzing section may be provided in at least one of the upper and lower plates.

In this case, the upper and lower plates may be composed of a transparent acryl resin or a polycarbonate resin containing an antistatic agent. The upper plate and/or the lower plate may be molded or machined in a predetermined configuration for formation of the quantifying section, the main channel and the analyzing section.

The upper plate and the lower plate may be combined together in an air-tight manner with the use of an adhesive, by an RF welding method or an ultraviolet bonding method, or by fixing the plates by means of screws with a rubber packing interposed between the plates.

In the inventive measuring unit, the main channel may have a bubble trapping portion for preventing a bubble from moving toward the quantifying section, or a rectifying portion for rectifying the transported sample.

The pressure introduction port may comprise a pipe projecting into the main channel.

In accordance with another aspect of the present invention, there is provided a rotary valve which comprises: an outer cylinder having an open bottom and a cylindrical inner circumferential surface; and an inner cylinder having a closed bottom and a recess provided in an outer circumferential surface thereof for quantifying a sample, the inner cylinder being fitted in the outer cylinder and rotatable about an axis thereof in sliding contact with the inner circumferential surface of the outer cylinder, the outer cylinder and the inner cylinder defining a diluent container for containing a diluent.

The rotary valve may further comprise a first channel for introducing the sample into the recess, and a second channel for allowing the recess to communicate with the diluent container, wherein the inner cylinder is rotated to open and close the first channel and the second channel.

In the rotary valve, the inner cylinder may be rotated to open the first channel for introducing the sample into the recess, to close the first channel for quantifying the sample, and to open the second channel for transporting the quantified sample into the diluent container for dilution of the sample.

Further, the present invention provides a measuring unit comprising an electrical resistance measuring section for measuring an electrical resistance of a sample, wherein the electrical resistance measuring section is detachably connected to an analyzer having a constant direct current source and a signal processing section.

The electrical resistance measuring section may comprise a channel for transporting a sample therethrough, a separation plate having a small through-hole and provided in the channel to obstruct the channel, and two electrodes exposed to the channel on opposite sides of the separation plate, the two electrodes being detachably connected to the analyzer.

The channel may have a rectifying portion for rectifying the transported sample.

The electrical resistance measuring section may have a space for retaining the measured sample.

The measuring unit may further include a quantifying section for quantifying the sample in volume; a main channel communicating between the quantifying section and the electrical resistance measuring section; and a pressure introduction port communicating with the main channel for introducing a pressure into the main channel to transport the sample from the quantifying section to the electrical resistance measuring section.

Embodiments

With reference to the attached drawings, the present invention will hereinafter be described in detail by way of embodiments thereof. However, it should be understood that the invention be not limited to these embodiments.

First Embodiment

1. Construction of Unit Body

Figure 2:
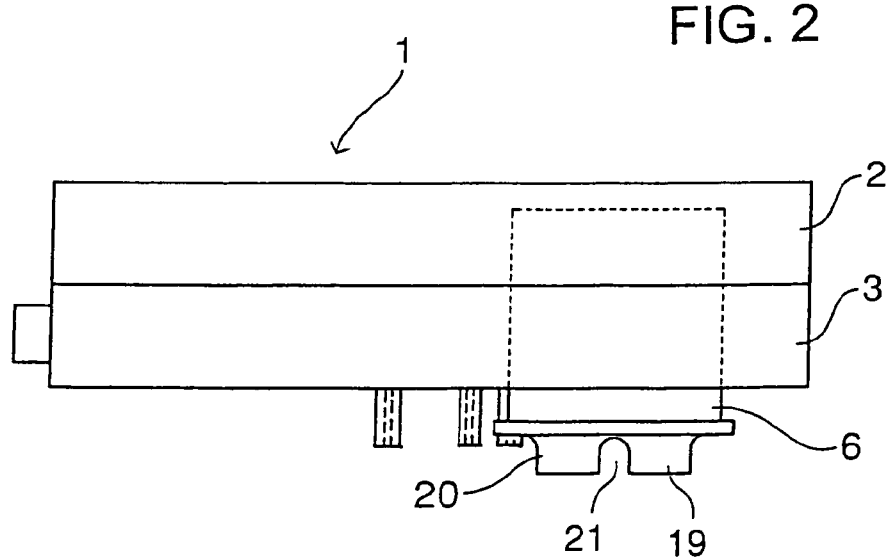
FIG. 2 is a front view of the measuring unit according to the first embodiment.
Figure 3:
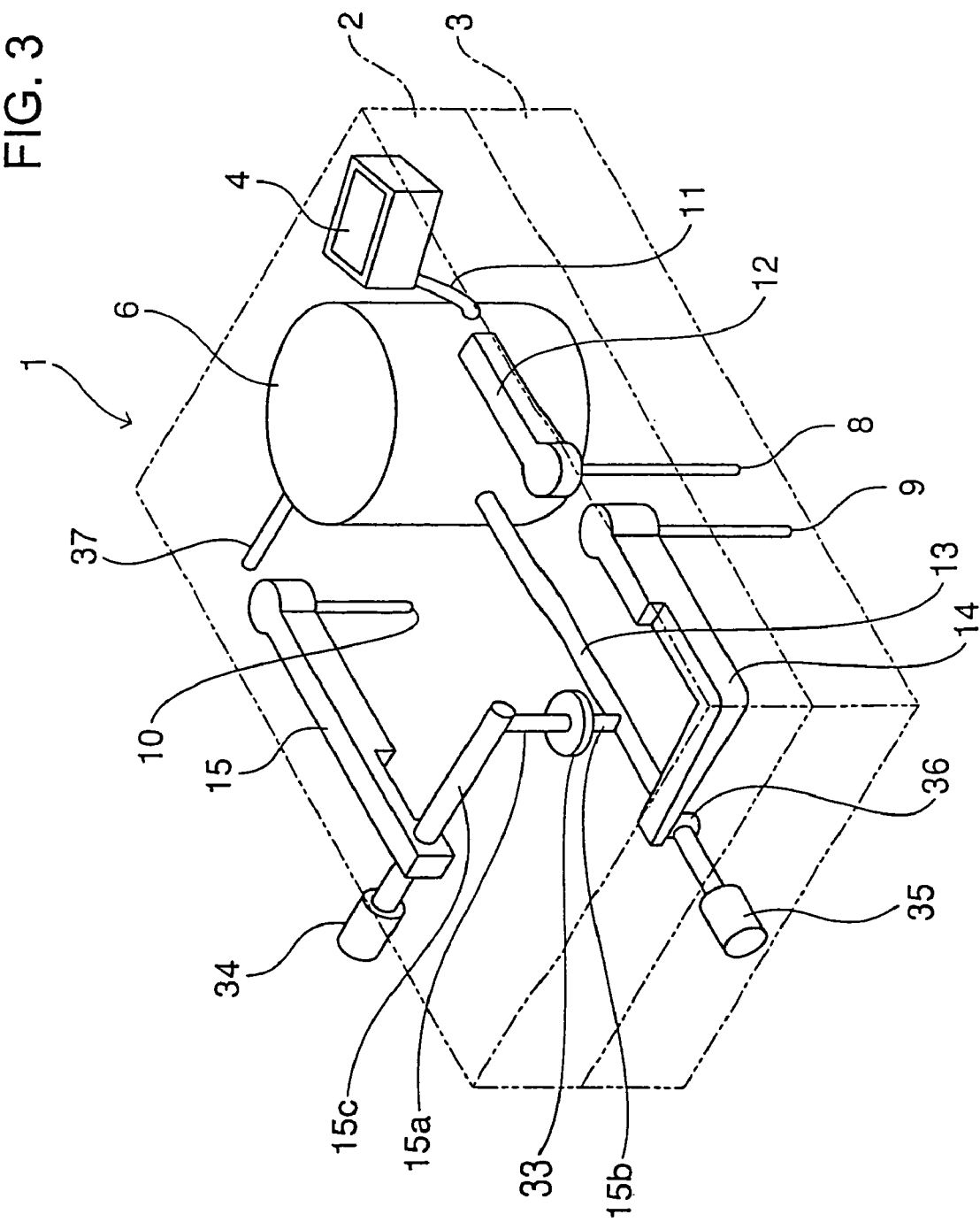
FIG. 3 is a perspective view illustrating the internal construction of the measuring unit according to the first embodiment.

FIGS. 1 and 2 are a top plan view and a front view, respectively, of a measuring unit according to a first embodiment of the invention. FIG. 3 is a perspective view illustrating the internal construction of the measuring unit.

As shown in FIGS. 1 to 3, a unit body 1 includes an upper plate 2 and a lower plate 3 composed of a transparent resin (e.g., an acryl resin or a polycarbonate resin containing an antistatic agent). The unit body 1 includes: a sample receiving section 4 having a volume of 200 μL for receiving a sample; a rotary valve 6 including a diluent container 5 incorporated therein, and having a sample quantifying function and a flow path switching function; an electrical resistance measuring section 7; and first, second and third pump connection ports 8, 9 and 10. The connection ports 8, 9, 10 are each constituted by a pipe projecting downward from the lower plate 3.

The sample receiving section 4 has a sample injection port provided on the top thereof, and the bottom thereof is connected to the rotary valve 6 via a channel 11. The pump connection port 8 is connected to the rotary valve 6 via a channel 12. The electrical resistance measuring section 7 is connected to the rotary valve 6 via a channel 13, to the pump connection port 9 via a channel 14, and to the pump connection port 10 via a channel 15. A vent hole 37 is provided for opening the rotary valve 6 to the atmosphere.

As will be described later in detail, the channels 11, 12 constitute a quantifying channel for introducing the sample into a sample quantifying section. The channel 13 constitutes a measuring channel for introducing a diluted sample from the diluent container 5 into the electrical resistance measuring section 7. Further, the channels 13, 14 constitute an agitation channel for agitating a mixture of the quantified sample and a diluent for preparation of the diluted sample. The channel 15 allows the electrical resistance measuring section 7 to communicate with the pump connection port 10, and constitutes a retention channel for retaining the diluted sample introduced therein after measurement.

Figure 35:
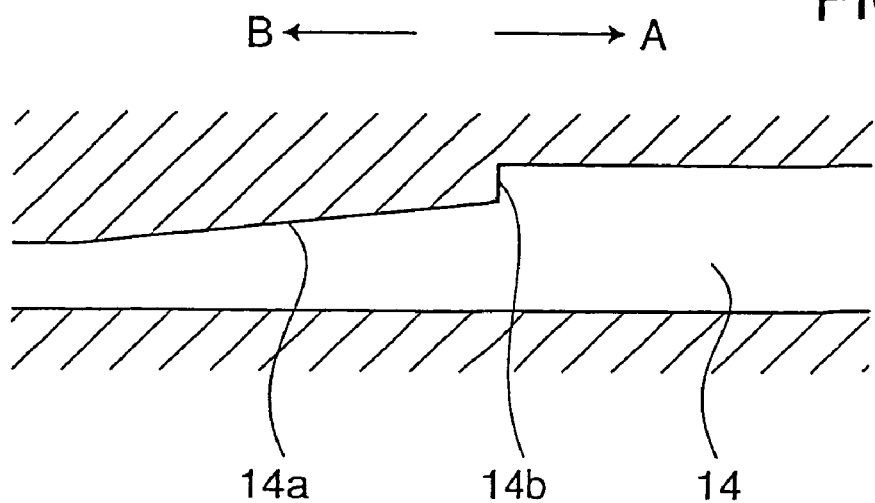
FIGS. 35 and 36 are sectional views illustrating major portions of a channel of the measuring unit shown in FIG. 3.

As shown in FIGS. 3 and 35, the channel 14 has a slant interior portion 14a and a stepped interior portion 14b, so that the sectional area thereof becomes greater toward the pump connection port 9. With this arrangement, bubbles generated when the mixture of the quantified sample and the diluent is moved back and forth in arrow directions A and B for agitation thereof are prevented from flowing back to the diluent container 5 (i.e., in the arrow direction B). Thus, the bubbles are prevented from being contained in the diluted sample.

Figure 36:
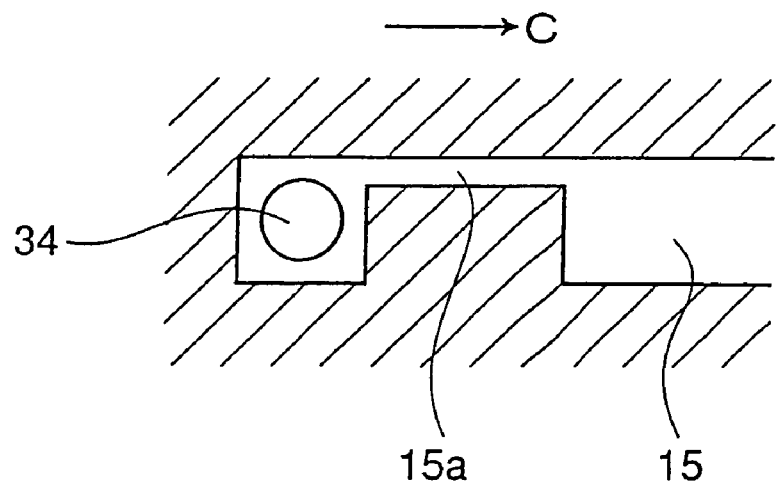

As shown in FIGS. 3 and 36, the channel 15 has a portion 15a having a sufficiently smaller sectional area than an internal channel 15c provided in the electrical resistance measuring section 7. With this arrangement, bubbles generated in the vicinity of an electrode (to be described later) of the electrical resistance measuring section 7 when a flow rate in the channel 15 is increased are sucked together with the diluted sample in an arrow direction C, so that the electrical resistance measuring section 7 is not influenced by the bubbles during the measurement.

2. Construction of Rotary Valve

Figure 4:
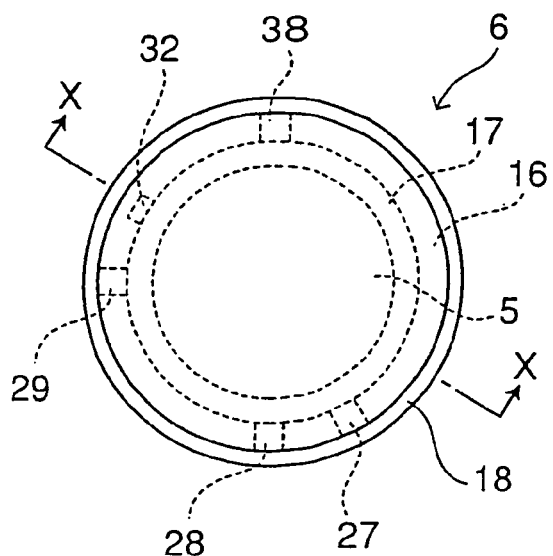
FIG. 4 is a top plan view of a rotary valve of the measuring unit according to the first embodiment.
Figure 5:
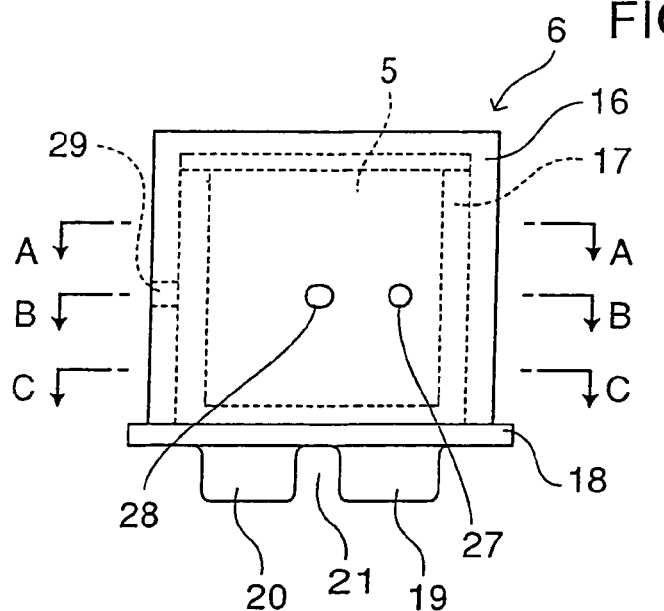
FIG. 5 is a front view of the rotary valve of the measuring unit according to the first embodiment.
Figure 6:
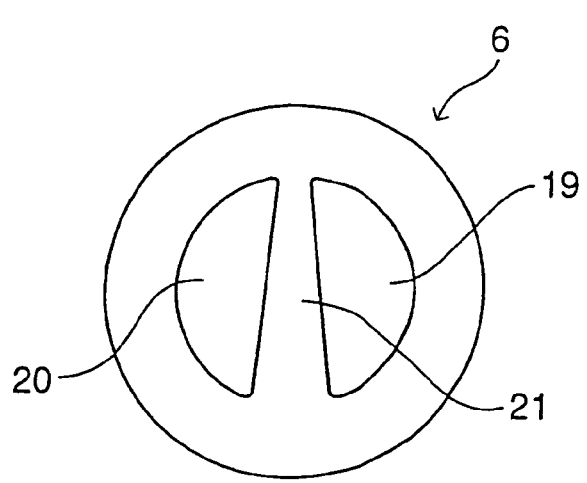
FIG. 6 is a bottom view of the rotary valve of the measuring unit according to the first embodiment.

FIGS. 4, 5 and 6 are a top plan view, a front view and a bottom view, respectively, of the rotary valve 6. As shown in FIGS. 4 to 6, the rotary valve 6 includes an outer cylinder 16 having an open bottom, and an inner cylinder 17 having a closed bottom and inserted in the outer cylinder 16 from the open bottom of the outer cylinder 16. The inner cylinder 17 has an open top, and a flange 18 provided at the bottom thereof.

Projections 19, 20 project downward from the flange 18 to define a groove 21 having non-parallel edges therebetween. The projections 19, 20 constitute a connector to be connected to a valve driving source to be described later. When the inner cylinder 17 is rotated about an axis thereof, an outer circumferential surface of the inner cylinder 17 is slidable in contact with an inner circumferential surface of the outer cylinder 16. Although the groove 21 has the non-parallel edges in this embodiment, the groove 21 may have parallel edges.

Figure 7:
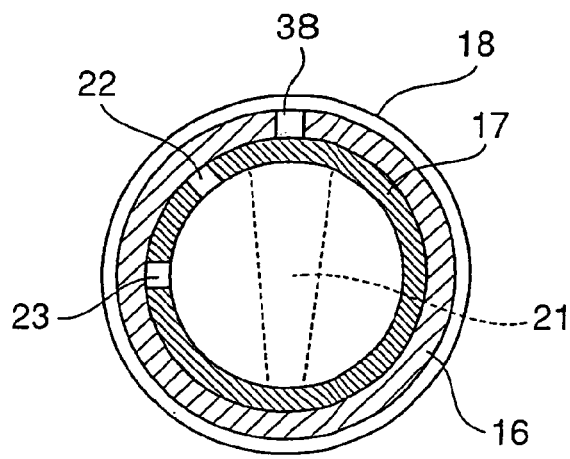
FIG. 7 is a sectional view of the rotary-valve as seen from an arrow direction A-A in FIG. 5.
Figure 8:
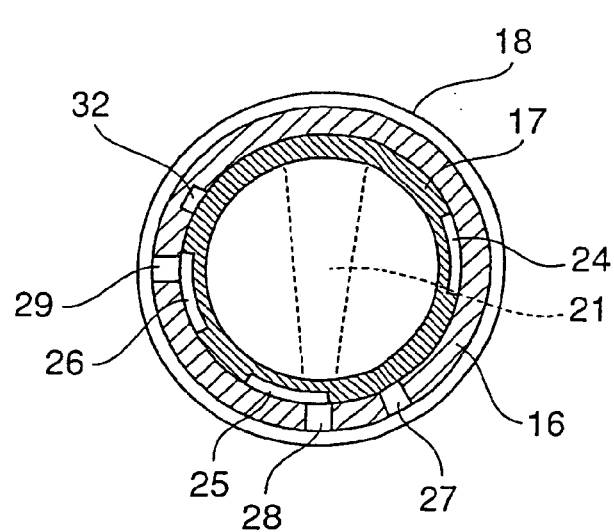
FIG. 8 is a sectional view of the rotary valve as seen from an arrow direction B-B in FIG. 5.
Figure 9:
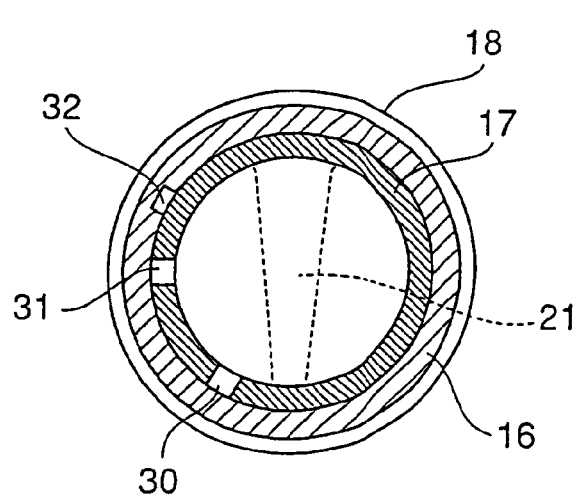
FIG. 9 is a sectional view of the rotary valve as seen from an arrow direction C-C in FIG. 5.
Figure 10:
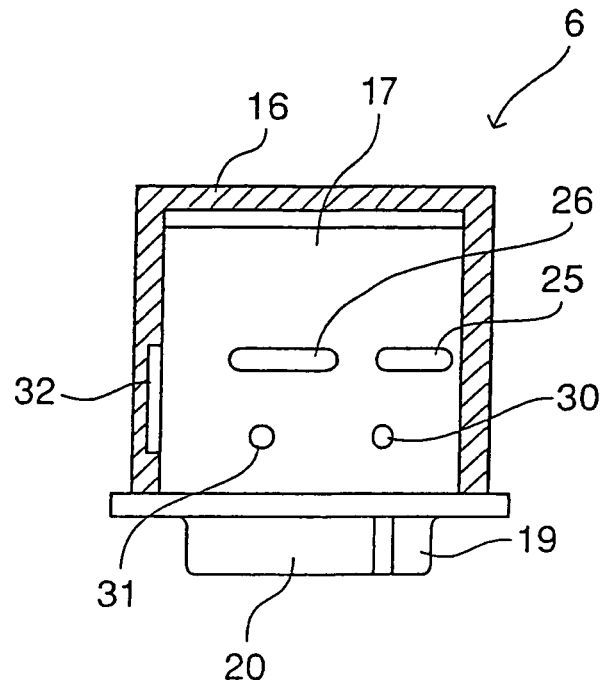
FIG. 10 is a sectional view of the rotary valve as seen from an arrow direction X-X in FIG. 4.

FIGS. 7, 8 and 9 are sectional views of the rotary valve 6 as seen in arrow directions A-A, B-B and C-C, respectively, in FIG. 5. FIG. 10 is a sectional view of the rotary valve 6 as seen in an arrow direction X-X in FIG. 4. As shown in FIG. 7, the inner cylinder 17 has two through-holes 22, 23 formed in an upper portion thereof for opening and closing the vent hole 37, and the outer cylinder 16 has a through-hole 38 communicating with the vent hole 37.

As shown in FIG. 8, the inner cylinder 17 has three elongated lateral grooves 24, 25, 26 formed in circumferentially aligned relation in a middle portion of the outer circumferential surface, and the outer cylinder 16 has three through-holes 27, 28 and 29 communicating with the channels 11, 12 and 13, respectively.

As will be described later, the lateral groove 25 serves as the sample quantifying section, and the lateral grooves 24, 26 serve as channel opening and closing grooves.

As shown in FIG. 9, the inner cylinder 17 has two through-holes 30, 31 formed in a lower portion thereof for channel opening and closing. As shown in FIGS. 8 to 10, the outer cylinder 16 further has an elongated vertical groove 32 formed in the inner circumferential surface thereof as extending axially from a middle portion to a lower portion thereof.

3. Construction of Electrical Resistance Measuring Section

As shown in FIGS. 1 and 3, the electrical resistance measuring section 7 includes a disk pellet 33 (separation plate) provided between vertical portions 15a and 15b of the internal channel 15c thereof, an electrode 34 provided in a junction between the channels 15 and 15c with an end thereof exposed to the inside of the channel and the other end thereof exposed to the outside of the upper plate 2, and an electrode 35 provided in a junction 36 between the channels 13 and 14 with an end thereof exposed to the inside of the channel and the other end thereof exposed to the outside of the lower plate 3.

Figure 11:
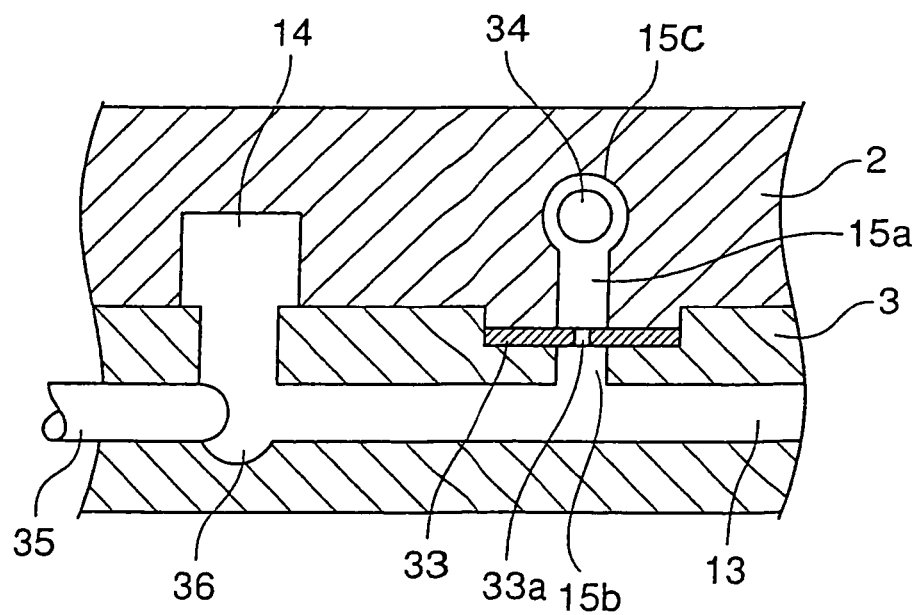
FIG. 11 is a sectional view illustrating a major portion of an electrical resistance measuring section of the measuring unit according to the first embodiment.

FIG. 11 is a sectional view illustrating a major portion of the electrical resistance measuring section 7. The pellet 33 is fitted in a round recess formed in the lower plate 3 coaxially with the vertical portion 15b and pressed by a round projection provided on the upper plate 2 coaxially with the vertical portion 15a.

The pellet 33 has a minute through-hole 33a formed in the center thereof, so that the electrical resistance of an electrolytic solution passing through the minute through-hole 33a is measured by the electrodes 34, 35. The pellet 33 is formed of a polyetherimide sheet having a thickness of 125 μm. The minute through-hole 33a is formed in the sheet as having a diameter of 100 μm by an excimer laser.

4. Analyzer

Figure 12:
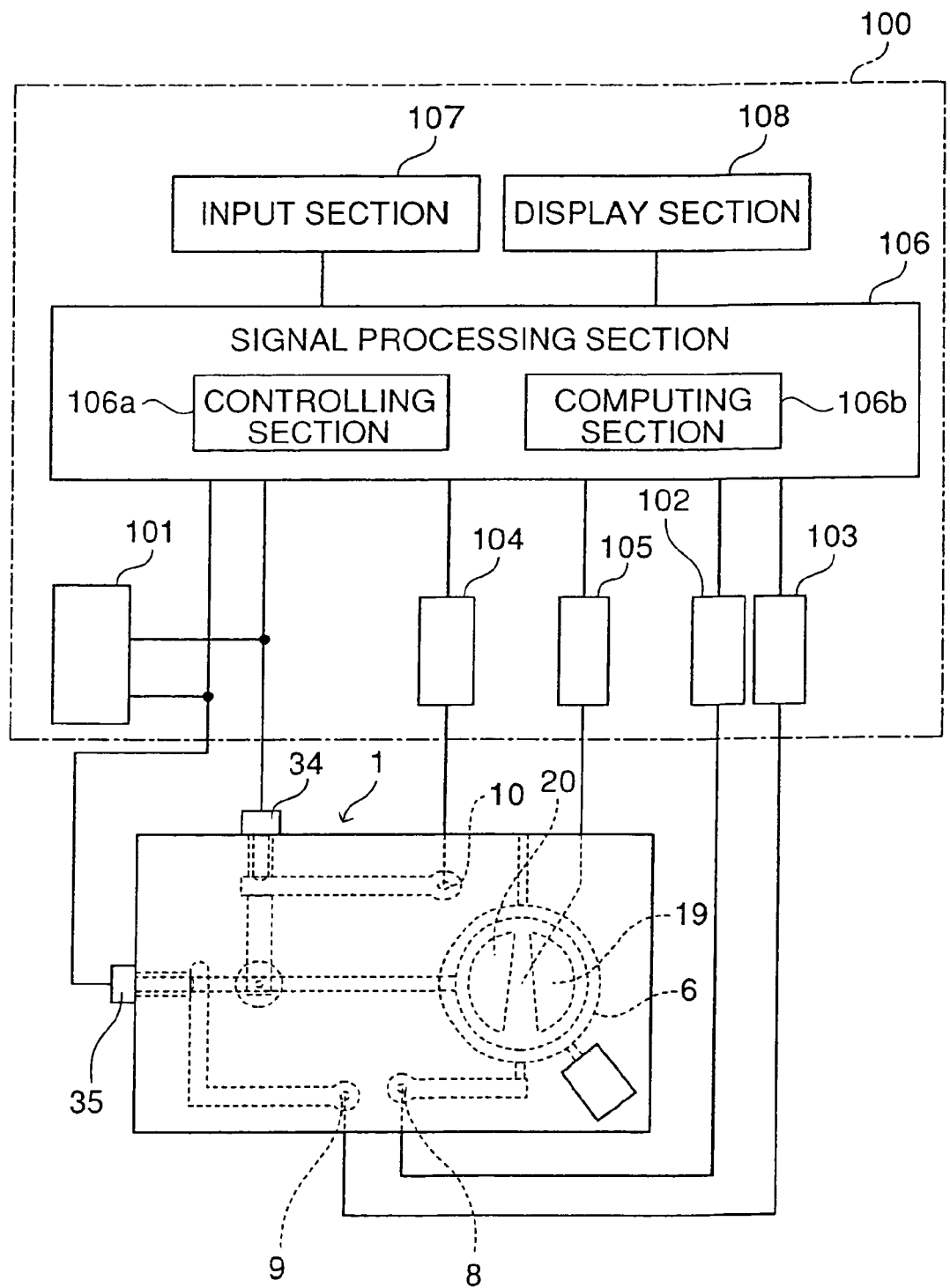
FIG. 12 is a block diagram illustrating the construction of an analyzer according to the first embodiment.

FIG. 12 is a block diagram illustrating the construction of an analyzer 100 which counts the number of white blood cells in a blood sample with the use of the unit body 1 for preparation of a particle size distribution. A constant direct current source 101 of the analyzer 100 is detachably connected to the exposed ends of the electrodes 34, 35 of the unit body 1, and electric syringe pumps 102, 103 and 104 are detachably connected to the first, second and third pump connection ports 8, 9 and 10, respectively. A stepping motor 105 for driving the valve 6 is detachably connected to the valve 6 via a connector (not shown) engaged with the groove 21 formed in the flange 18 at the bottom of the valve 6.

A signal processing section 106 includes a controlling section 106a and a computing section 106b, which are comprised of a microprocessor. The controlling section 106a drives the electric syringe pumps 102, 103, 104 and the stepping motor 105 in response of a command applied thereto from an input section 107. The computing section 106b counts the number of the white blood cells and calculates the size of each of the white blood cells on the basis of signals applied from the electrodes 34, 35. The results are displayed on a display section 108.

5. Measuring Operation

Figure 13:
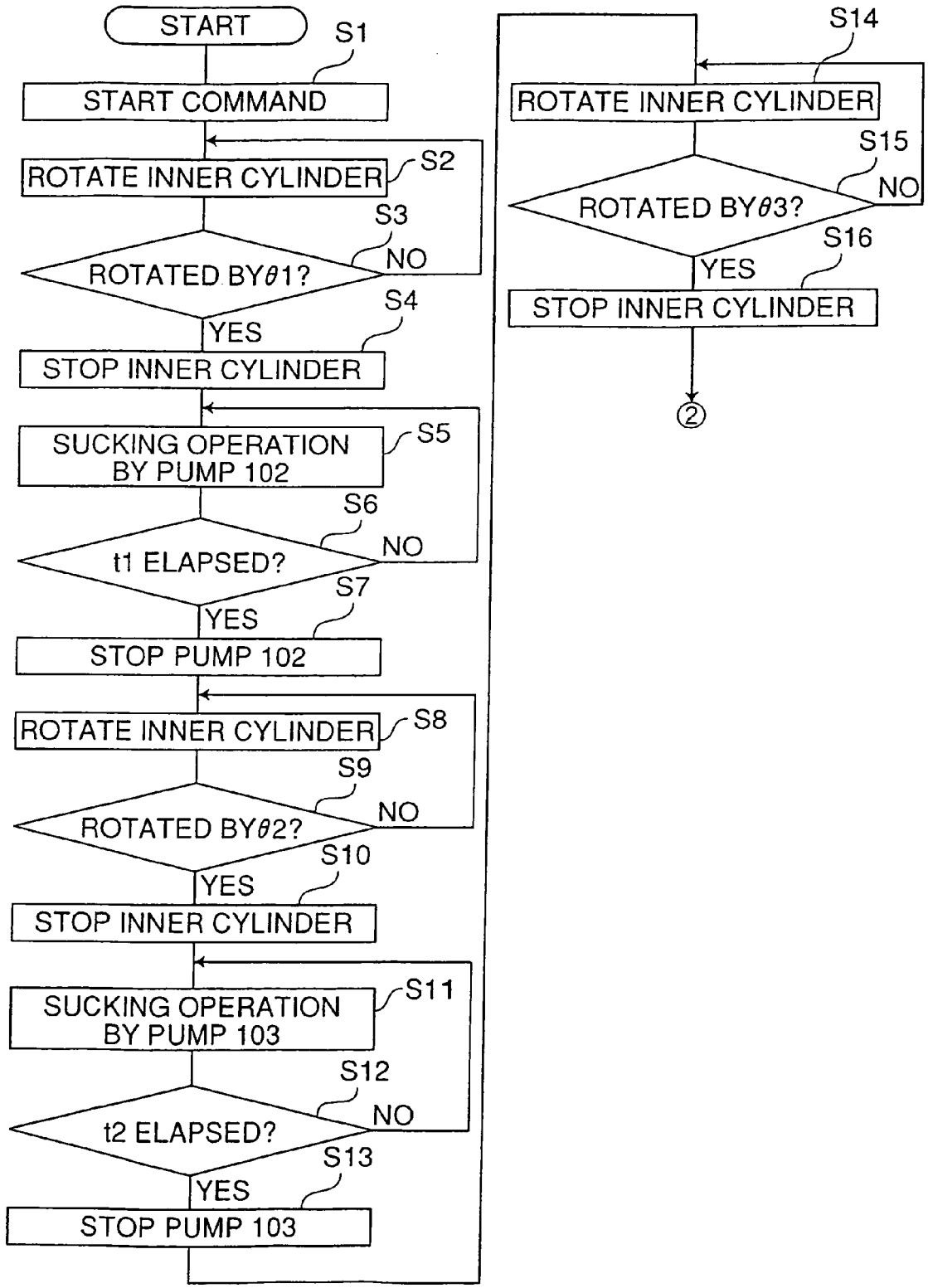
FIGS. 13 to 15 are flow charts for explaining the operation of the analyzer of FIG. 12.
Figure 14:
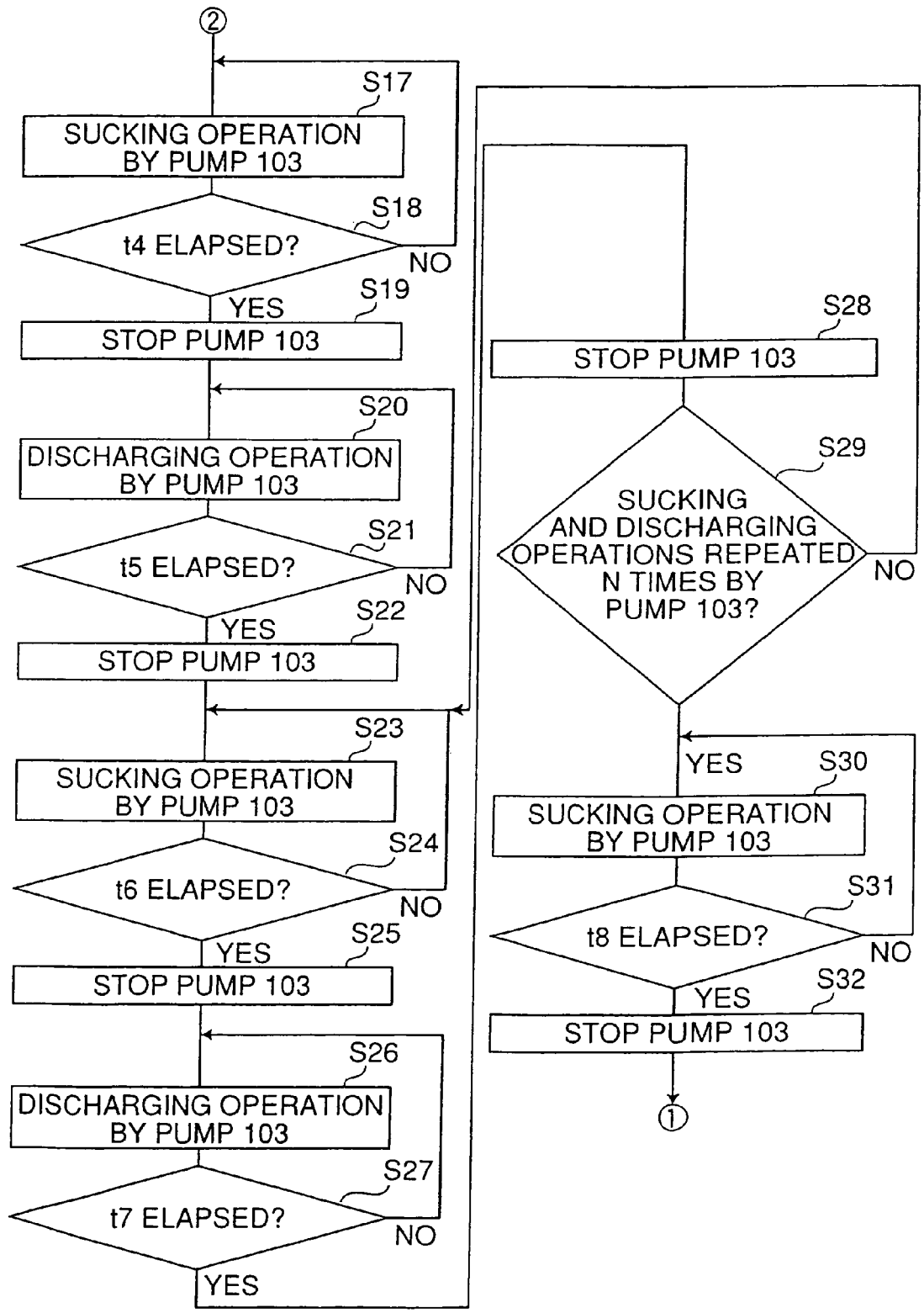
Figure 15:
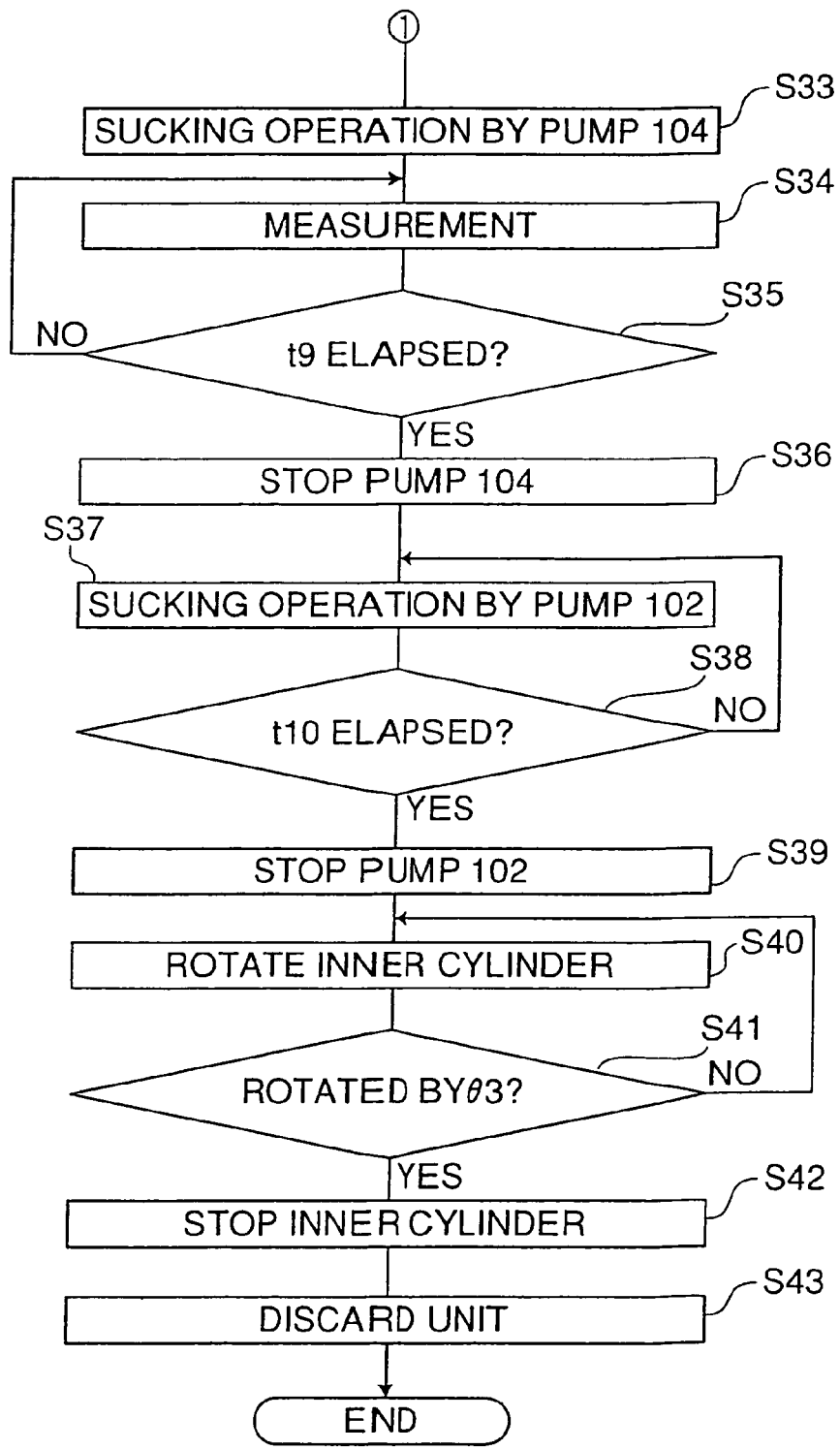
Figure 16:
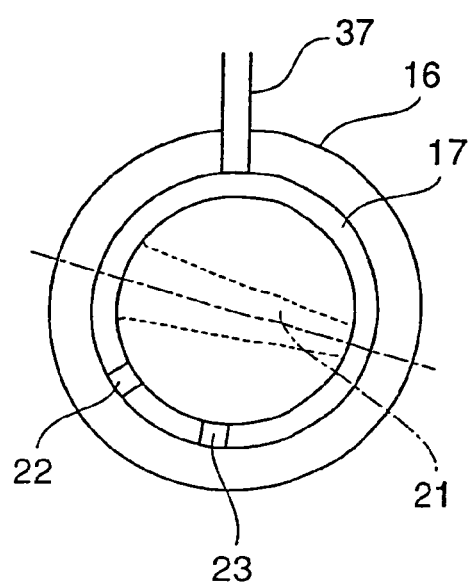
FIGS. 16(a) to 16(c) are diagrams for explaining the operation of the rotary valve of the measuring unit according to the first embodiment.
Figure 16:
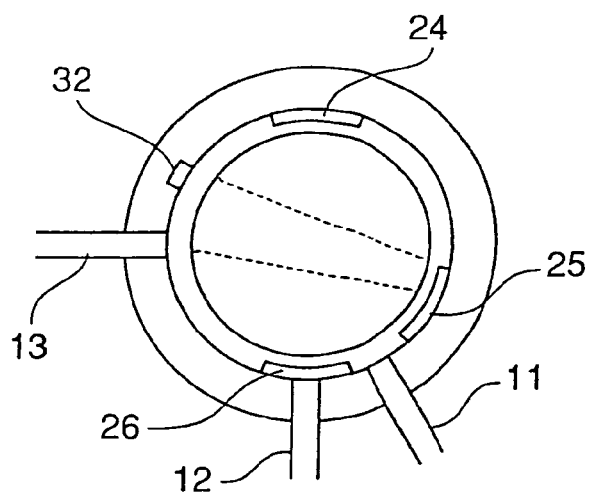
Figure 16:
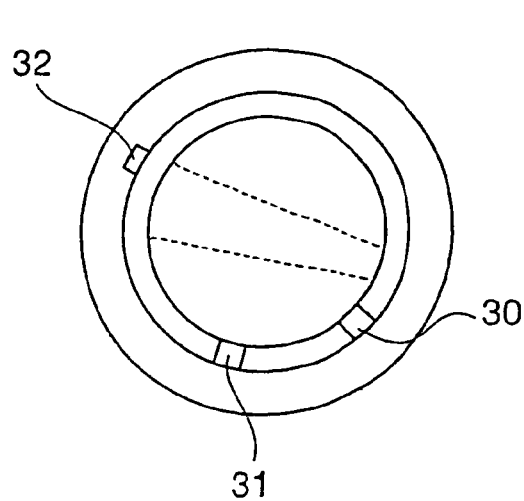
Figure 17:
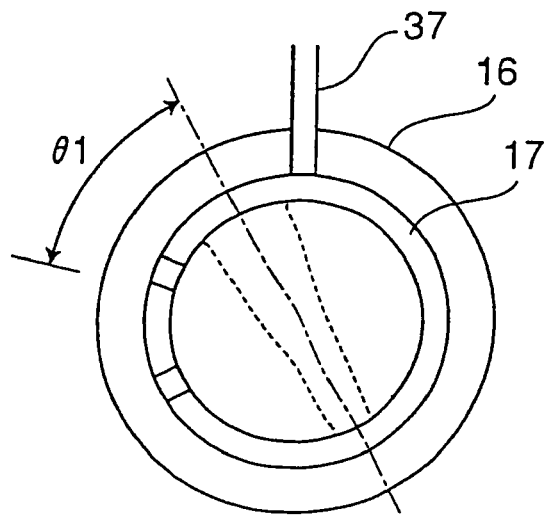
FIGS. 17(a) to 17(c) are diagrams for explaining the operation of the rotary valve of the measuring unit according to the first embodiment.
Figure 17:
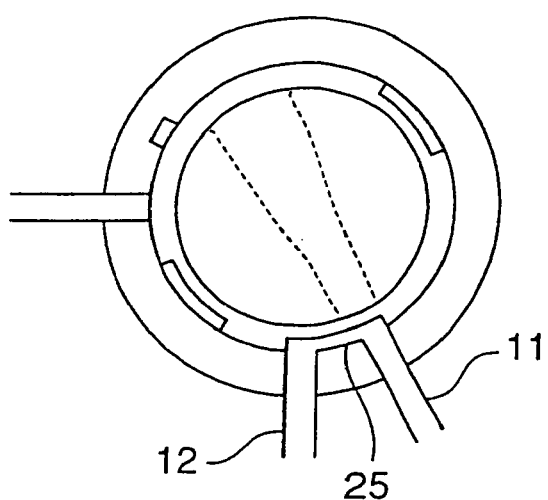
Figure 17:
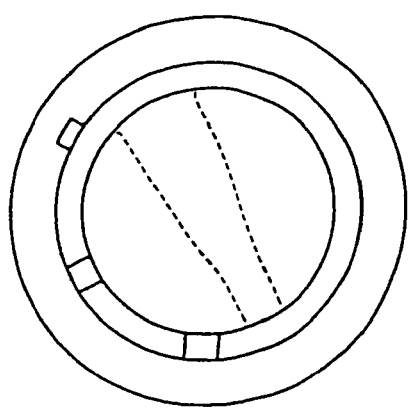
Figure 18:
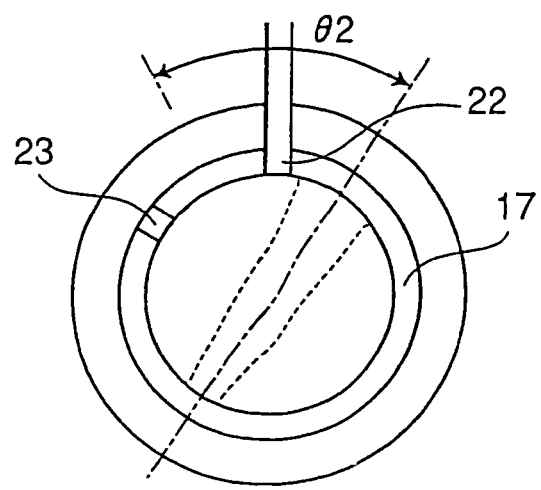
FIGS. 18(a) to 18(c) are diagrams for explaining the operation of the rotary valve of the measuring unit according to the first embodiment.
Figure 18:
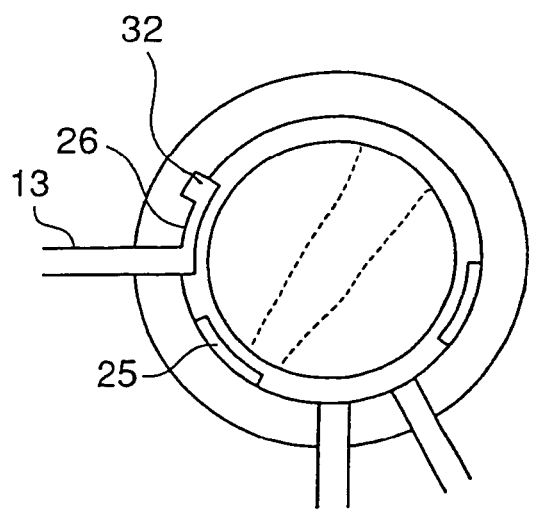
Figure 18:
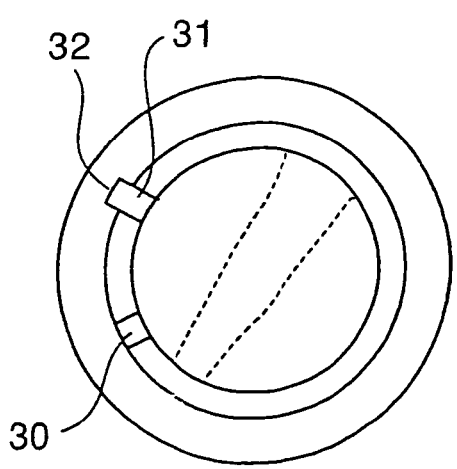
Figure 19:
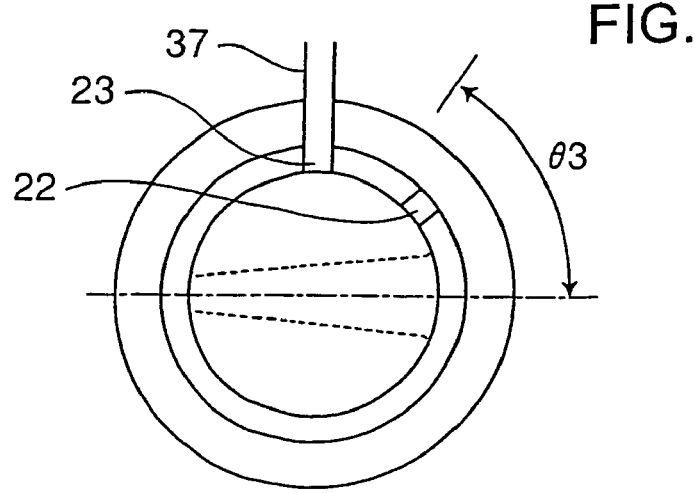
FIGS. 19(a) to 19(c) are diagrams for explaining the operation of the rotary valve of the measuring unit according to the first embodiment.
Figure 19:
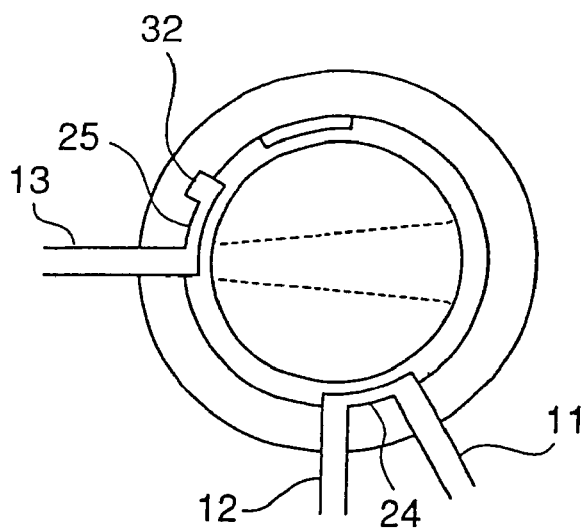
Figure 19:
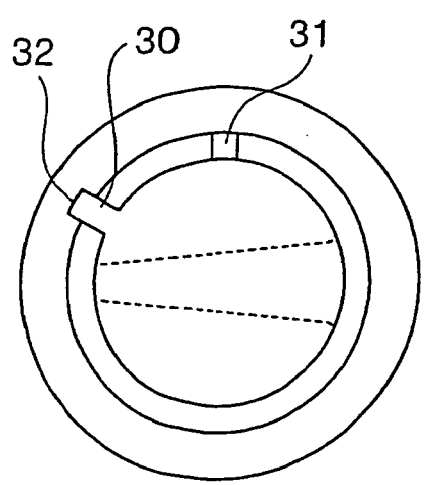
Figure 20:
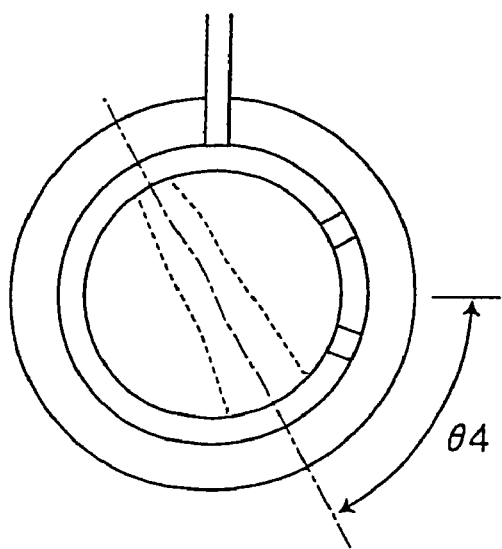
FIGS. 20(a) to 20(c) are diagrams for explaining the operation of the rotary valve of the measuring unit according to the first embodiment.
Figure 20:
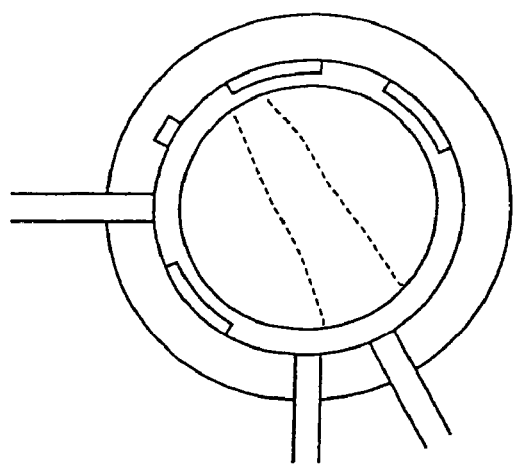
Figure 20:
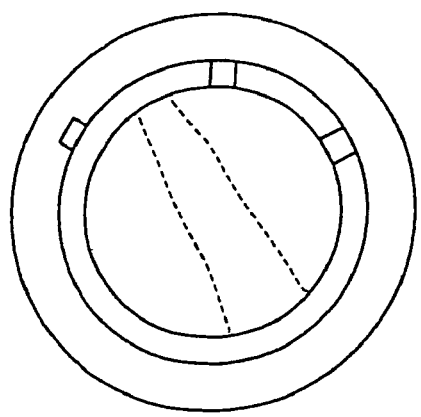

With reference to flow charts shown in FIGS. 13 to 15, an explanation will hereinafter be given to the operation of the analyzer 100 shown in FIG. 12. FIGS. 16(a) to 16(c), 17(a) to 17(c), 18(a) to 18(c), 19(a) to 19(c) and 20(a) to 20(c) illustrate rotational positions of the inner cylinder 17 with respect to the outer cylinder 16 of the rotary valve 6. Particularly, FIGS. 16(a) to 20(a), FIGS. 16(b) to 20(b), FIGS. 16(c) to 20(c) are sectional views of the rotary valve 6 as seen in arrow directions A-A, B-B and C-C, respectively, in FIG. 5.

In the unit body 1, the rotary valve 6 retains 1,000 μL of the diluent (a mixture of a dilution agent and a hemolyzing agent) preliminarily quantified in the diluent container 5. The inner cylinder 17 is initially in a rotational position as shown in FIGS. 16(a) to 16(c) with respect to the outer cylinder 16, so that the diluent L is confined in the container 5 as shown in FIG. 21.

Figure 21:
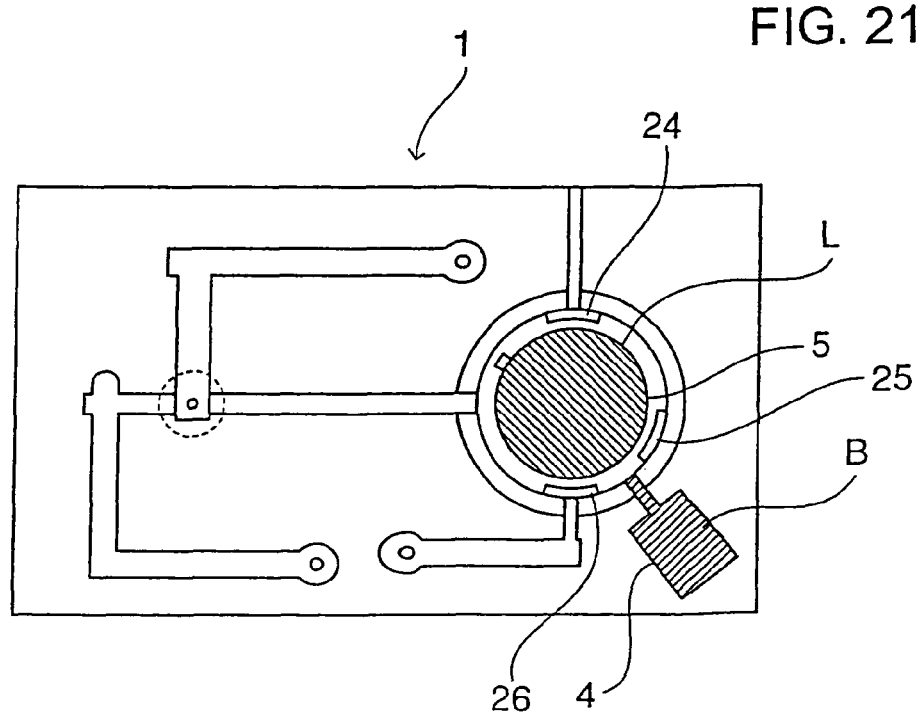
FIGS. 21 to 34 are diagrams for explaining the movement of a sample and a diluent in the measuring unit according to the first embodiment.

The unit body 1 is connected to the analyzer 100 as shown in FIG. 12, and about 10 μL to about 150 μL of a whole blood sample B is injected into the sample receiving section 4 by a syringe or a pipette as shown in FIG. 21.

When a start command is applied from the input section 107 (FIG. 12) (Step S1), the stepping motor 105 is driven so that the inner cylinder 17 is rotated clockwise by an angle θ1 (Steps S2 to S4) thereby to reach a position as shown in FIGS. 17(a) to 17(c) and 22.

Figure 22:
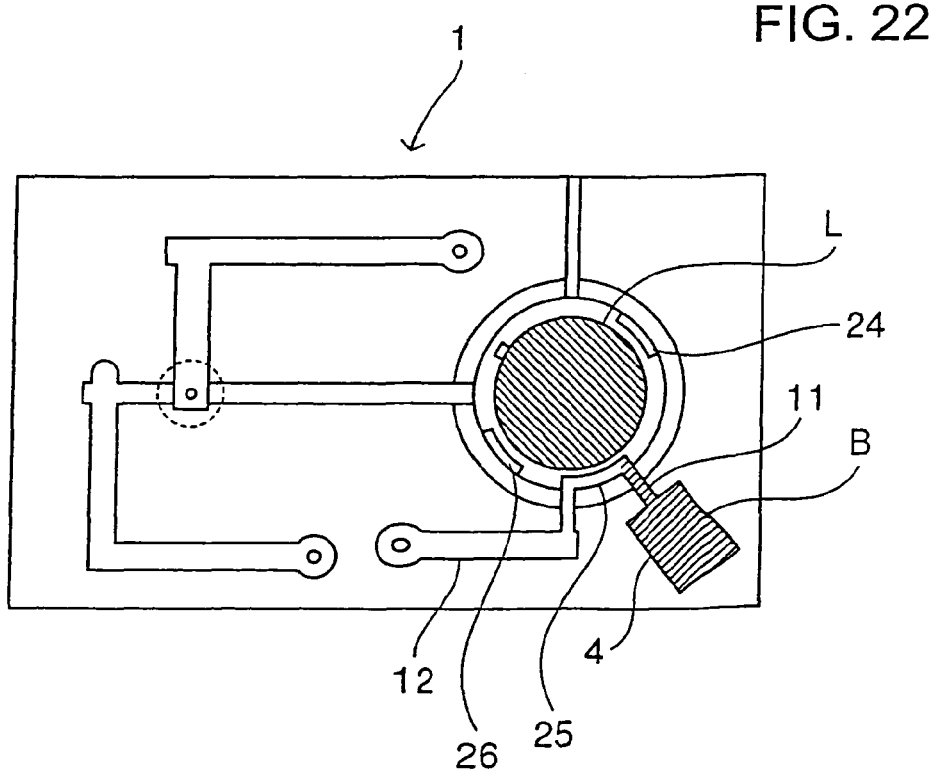
Figure 23:
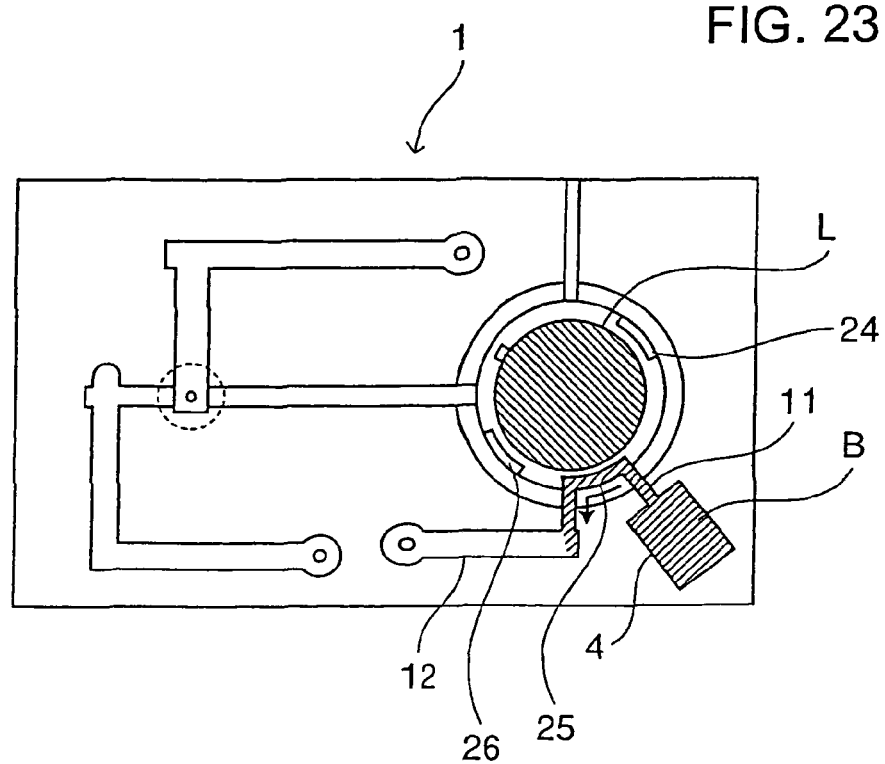

Thus, the channels 11, 12 communicate with each other via the lateral groove 25 to form the quantifying channel as shown in FIGS. 17(b) and 22. In this state, the syringe pump 102 performs a sucking operation for a time period t1 (Steps S5 to S7), whereby the sample B flows into the channel 12 from the sample receiving section 4 via the lateral groove 25 to fill the lateral groove 25 as shown in FIG. 23.

Figure 24:
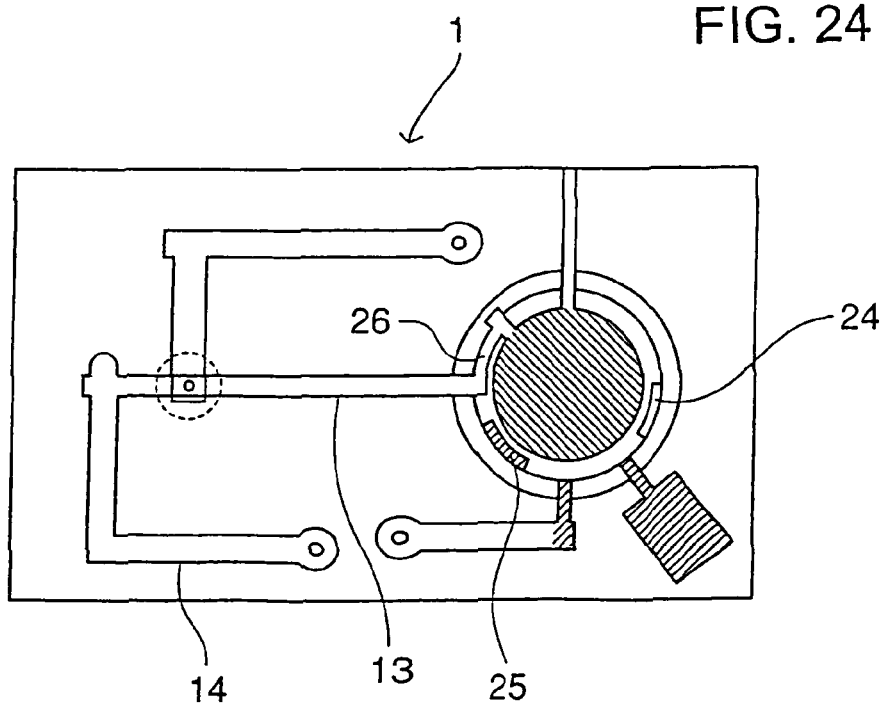

In turn, the stepping motor 105 is driven so that the inner cylinder 17 is rotated clockwise by an angle θ2 (Steps S8 to S10) thereby to reach a position as shown in FIGS. 18(a) to 18(c) and 24. Thus, the sample is quantified in a volume of 2 μm which is equivalent to the volume of the lateral groove 25, and separated by the inner circumferential surface of the outer cylinder 16 as shown in FIG. 24.

At the same time, the through-hole 22 of the inner cylinder 17 communicates with the vent hole 37 to open an upper portion of the diluent container 5 to the atmosphere as shown in FIG. 18(a), and the channel 13 communicates with the bottom of the diluent container 5 via the lateral groove 26, the vertical groove 32 and the through-hole 31 as shown in FIGS. 18(b) and 18(c).

Figure 25:
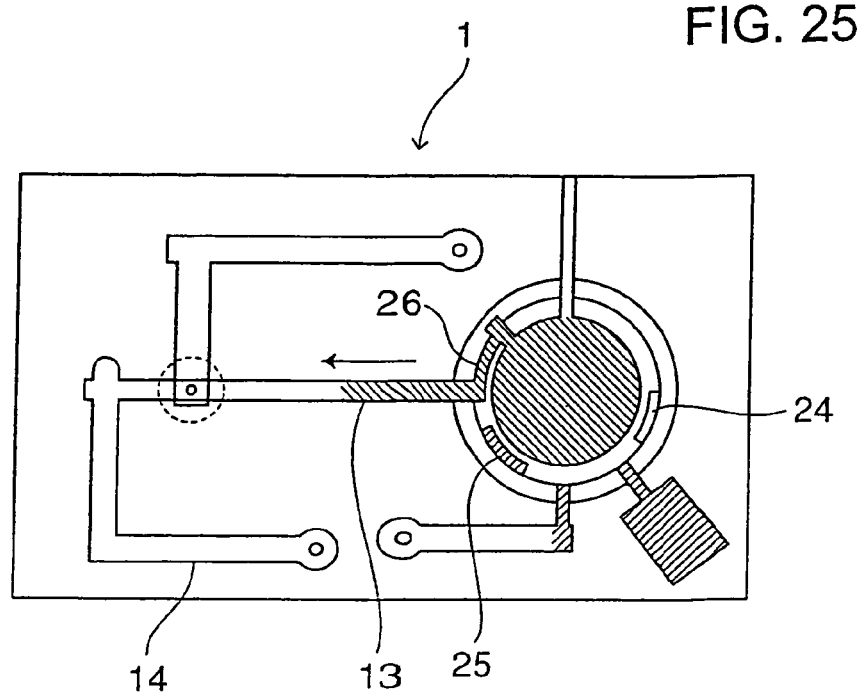

Then, the syringe pump 103 performs a sucking operation for a time period t2 (Steps S11 to S13), whereby the diluent L is introduced into the channel 13 from the diluent container 5 as shown in FIG. 25.

Subsequently, the stepping motor 105 is driven so that the inner cylinder 17 is rotated clockwise by an angle θ3 (Steps S14 to S16) thereby to reach a position as shown in FIGS. 19(a) to 19(c).

Figure 26:
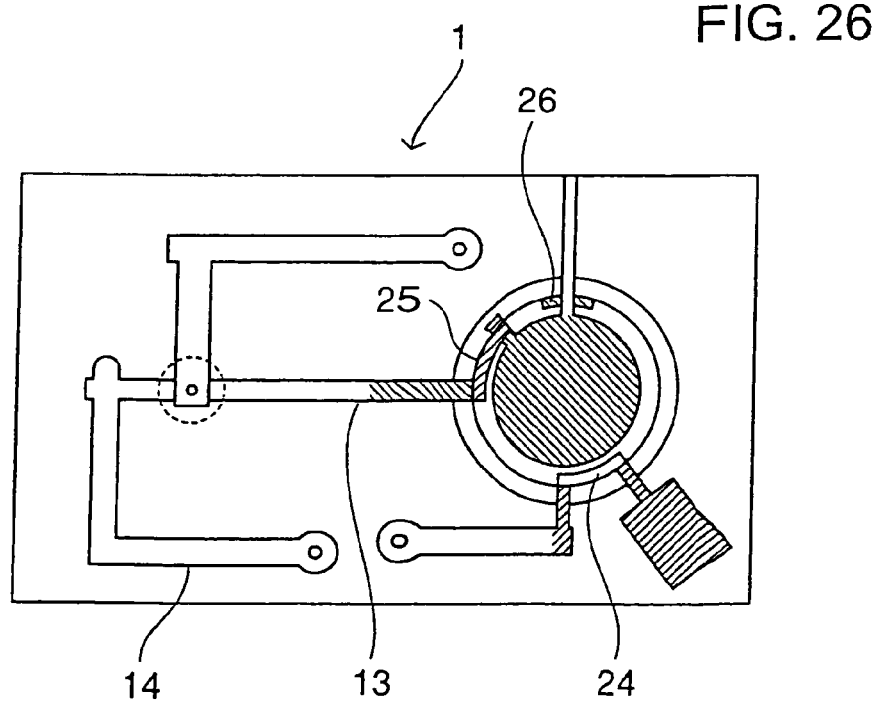

Thus, the through-hole 23 of the inner cylinder 17 communicates with the vent hole 37 to open the upper portion of the diluent container 5 to the atmosphere as shown in FIG. 19(a), and the channel 13 communicates with the bottom of the diluent container 5 via the lateral groove 25, the vertical groove 32 and the through-hole 30 to form the agitation channel as shown in FIGS. 19(b), 19(c) and 26. At the same time, the channel 11 communicates with the channel 12 via the lateral groove 24 as shown in FIG. 19(b).

Figure 27:
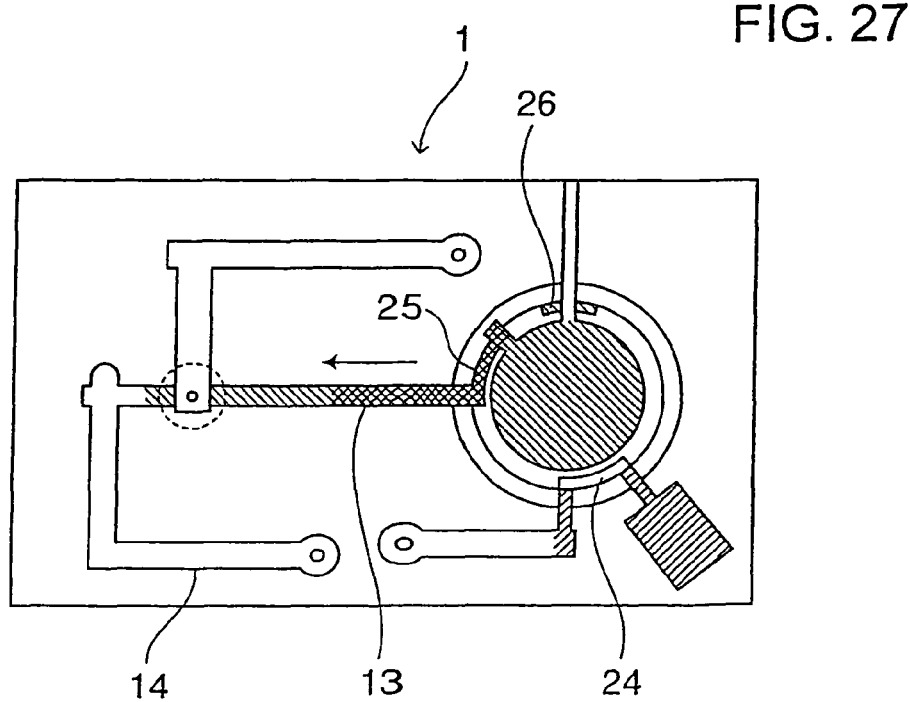

Then, the syringe pump 103 further performs the sucking operation for a time period t4 (Steps S17 to S19), whereby the diluent in the diluent container 5 and the quantified sample in the lateral groove 25 are introduced into the channel 13 as shown in FIG. 27.

Figure 28:
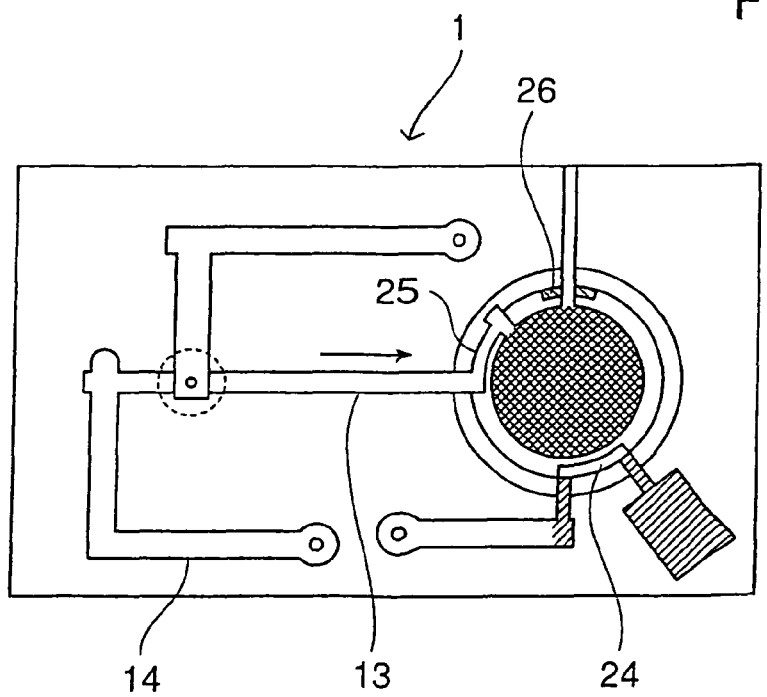

In turn, the syringe pump 103 performs a discharging operation for a time period t5 (Steps S20 to S22), whereby the sample and the diluent are fed back into the diluent container 5 as shown in FIG. 28.

Figure 29:
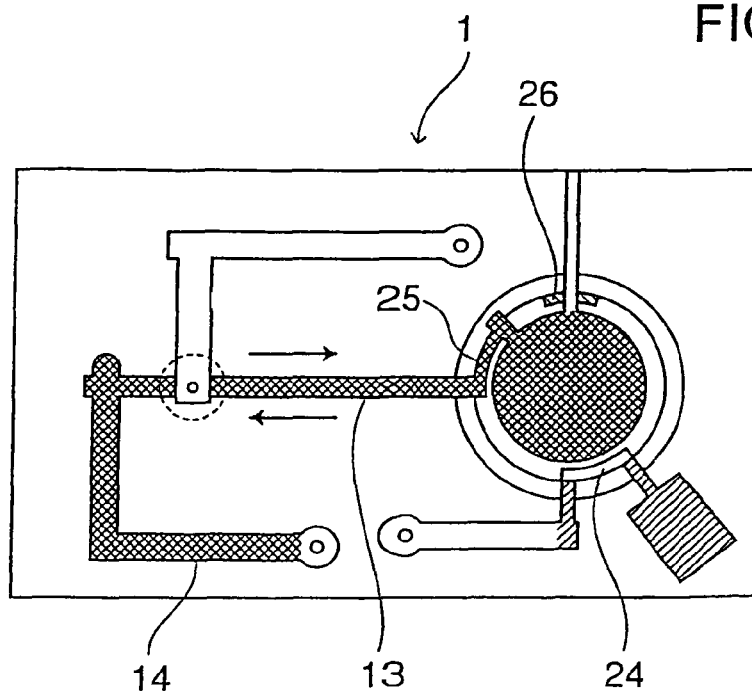
Figure 30:
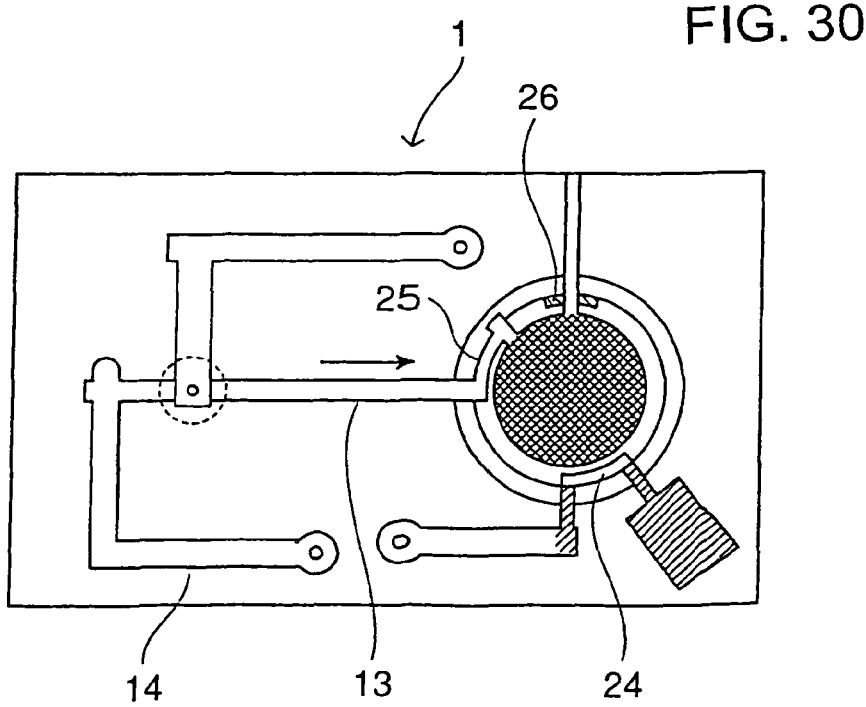

Subsequently, the syringe pump 103 repeats a t6-period sucking operation and a t7-period discharging operation N times (Steps S23 to S29), whereby the diluent and the sample flow back and forth between the channels 13, 14 and the diluent container 5 as shown in FIG. 29. Thus, the diluent and the sample are sufficiently mixed and agitated for preparation of a 500-time diluted sample. The diluted sample is retained in the diluent container 5 as shown in FIG. 30.

Figure 31:
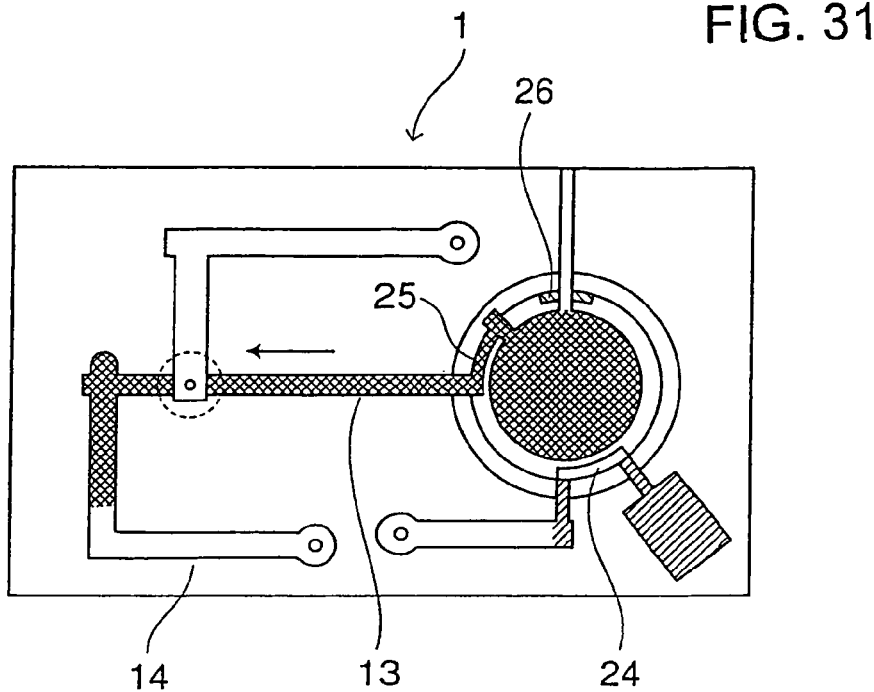

Then, the syringe pump 103 performs the sucking operation for a time period t8 (Steps S30 to S32), whereby the diluted sample is introduced into the channels 13, 14 from the diluent container 5 as shown in FIG. 31.

Figure 32:
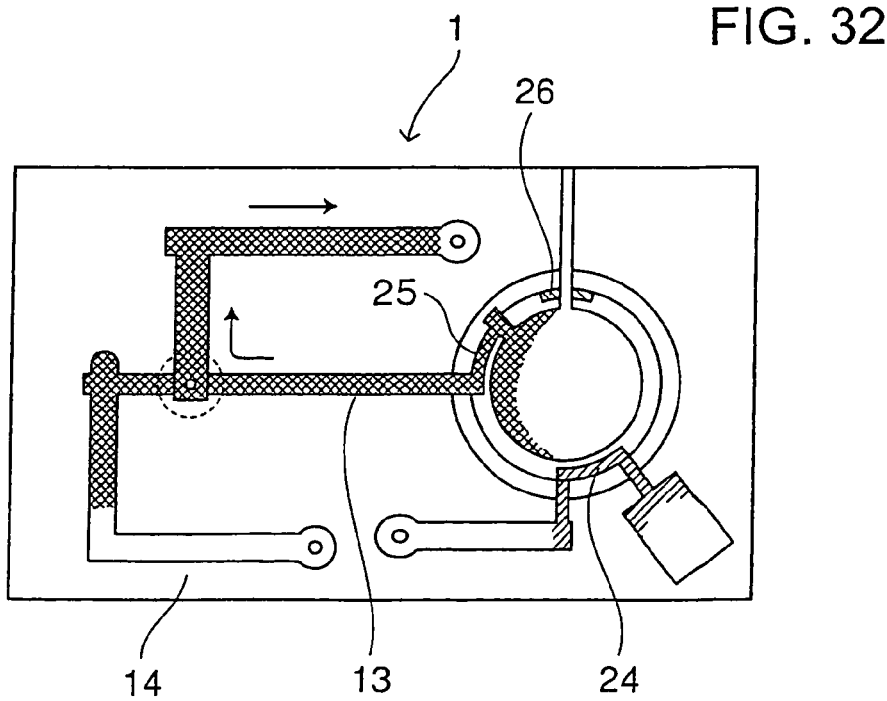

In turn, the syringe pump 104 performs a sucking operation for a time period t9, whereby the diluted sample flows toward the syringe pump 104 from the diluent container 5 via the channel 13, the pellet 33 and the channel 15 (i.e., via the measuring channel) as shown in FIG. 32. During this period, the signal processing section 106b measures an electrical resistance between the electrodes 34 and 35 (Steps S33 to S36).

Figure 33:
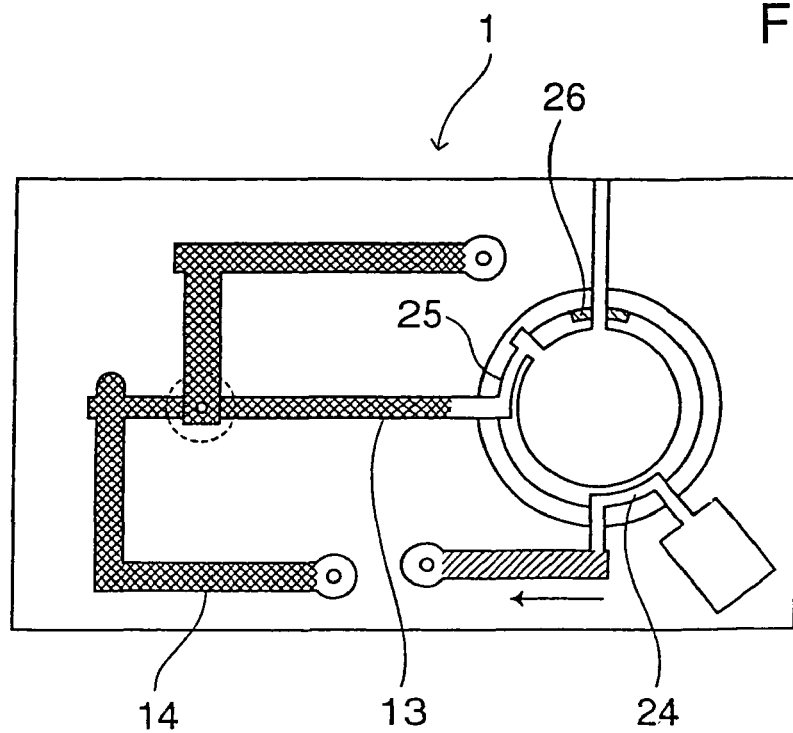

Subsequently, the syringe pump 102 performs the sucking operation for a time period t10 (Steps S37 to S39), whereby all the sample remaining in the sample receiving section 4 is retained in the channel 12 as shown in FIG. 33. On the other hand, all the diluted sample in the diluent container 5 is retained in the channels 13, 14, 15 in Steps S33 to S36.

Figure 34:
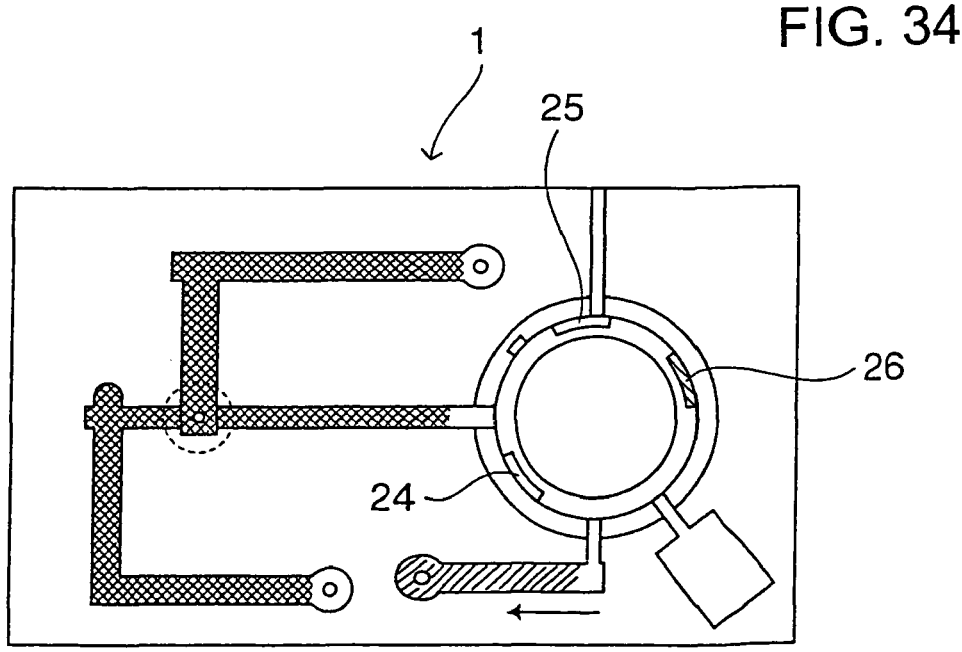

In turn, the stepping motor 105 is driven so that the inner cylinder 17 is rotated clockwise by an angle θ4 (Steps S40 to S42) thereby to reach a position as shown in FIGS. 20(a) to 20(c). Thus, the vent hole 37 and the channel 11 are brought out of communication with the diluent container 5 and the channel 12, respectively, as shown in FIG. 34.

In the aforesaid manner, the measuring operation is completed with the residual sample retained in the channel 12 and with the diluted sample retained in the channels 13 to 15, so that the residual sample and the diluted sample do not leak out of the unit body 1. Thereafter, the unit body 1 is removed from the analyzer 100 and discarded (Step S43).

6. Count of Number of Particles and Calculation of Particle Diameter

When the constant current from the constant direct current source 101 (FIG. 12) is applied to the diluted sample between the electrodes 34 and 35 in a space separated by the pellet 33 having the minute through-hole 33a as shown in FIG. 11, the electrical resistance between the electrodes 34 and 35 generally depends on the specific resistivity of a liquid component of the diluted sample. Particularly, the electrical resistance is determined by an electrical resistance of the liquid component present in and around the minute through-hole 33a, mainly depending on the diameter of the minute through-hole 33a and the thickness of the pellet 33.

When a particle (white blood cell) passes through the minute through-hole 33a, the liquid component is removed by the volume of the particle, so that the electrical resistance between the electrodes 34 and 35 changes. A change in the electrical resistance is detected as a voltage pulse generated between the electrodes 34 and 35.

Therefore, the computing section 106b determines the number of particles (white blood cells) on the basis of the number of pulses. Since the amplitude of the pulse is proportional to the volume of the particle, the computing section 106b detects the amplitude of each pulse, and calculates the spherical equivalent diameter of each particle (white blood cell) for preparation of a particle size distribution diagram.

Where red blood cells or platelets are subjected to the particle analysis, the volume of the diluent container 5 according to this embodiment is increased (for example, the sample is diluted 25,000 times), and a diluent not containing the hemolyzing agent is employed as the diluent.

Second Embodiment

1. Construction of Unit Body

Figure 37:
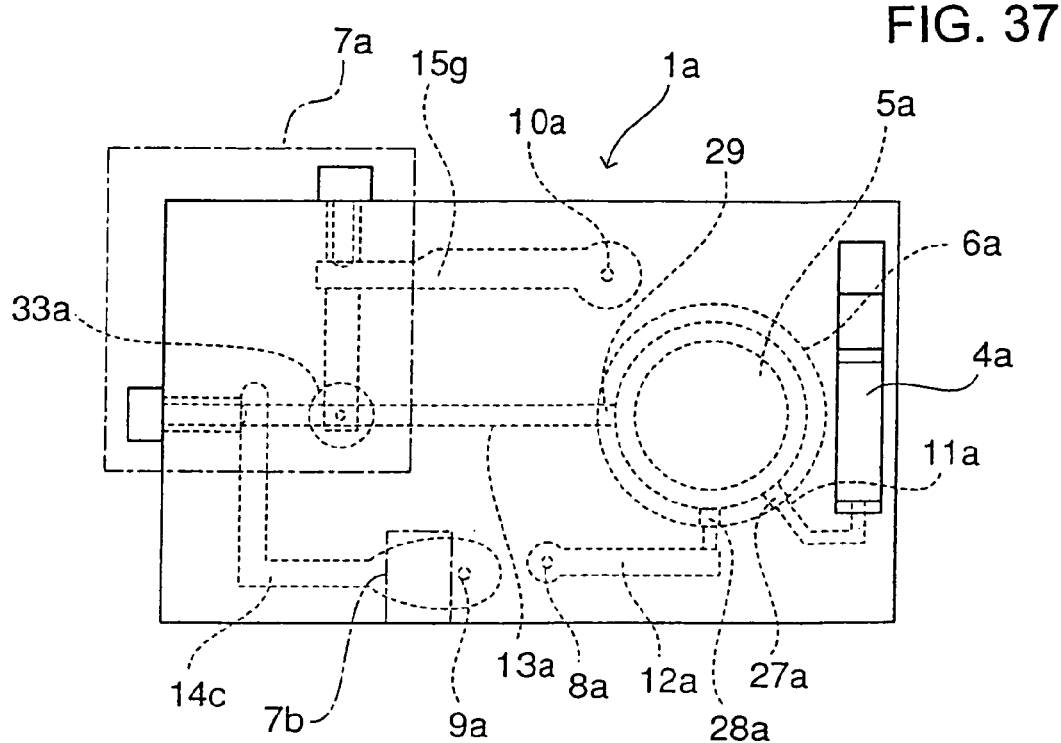
FIG. 37 is a top plan view of a measuring unit according to a second embodiment of the present invention.
Figure 38:
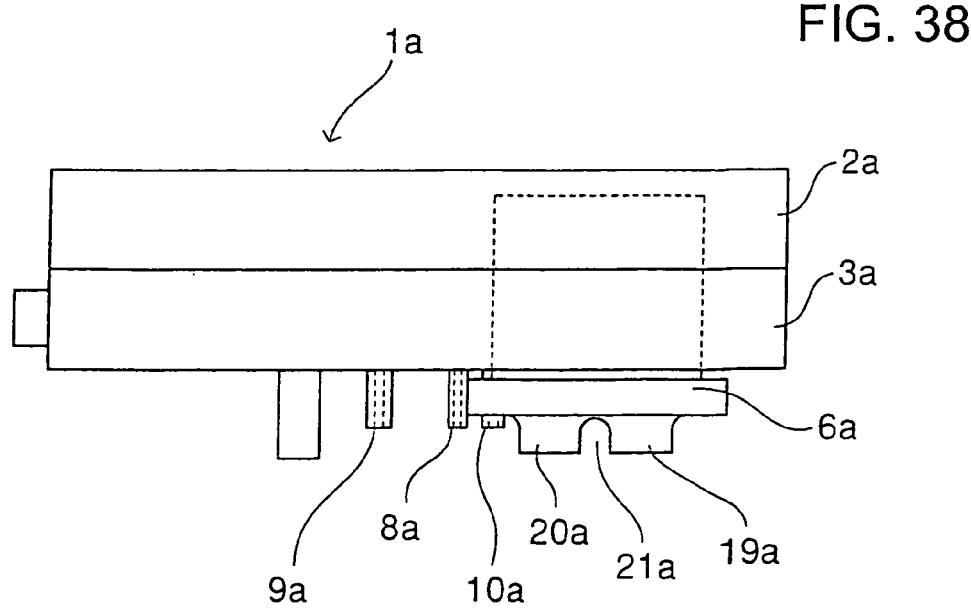
FIG. 38 is a front view of the measuring unit according to the second embodiment.
Figure 39:
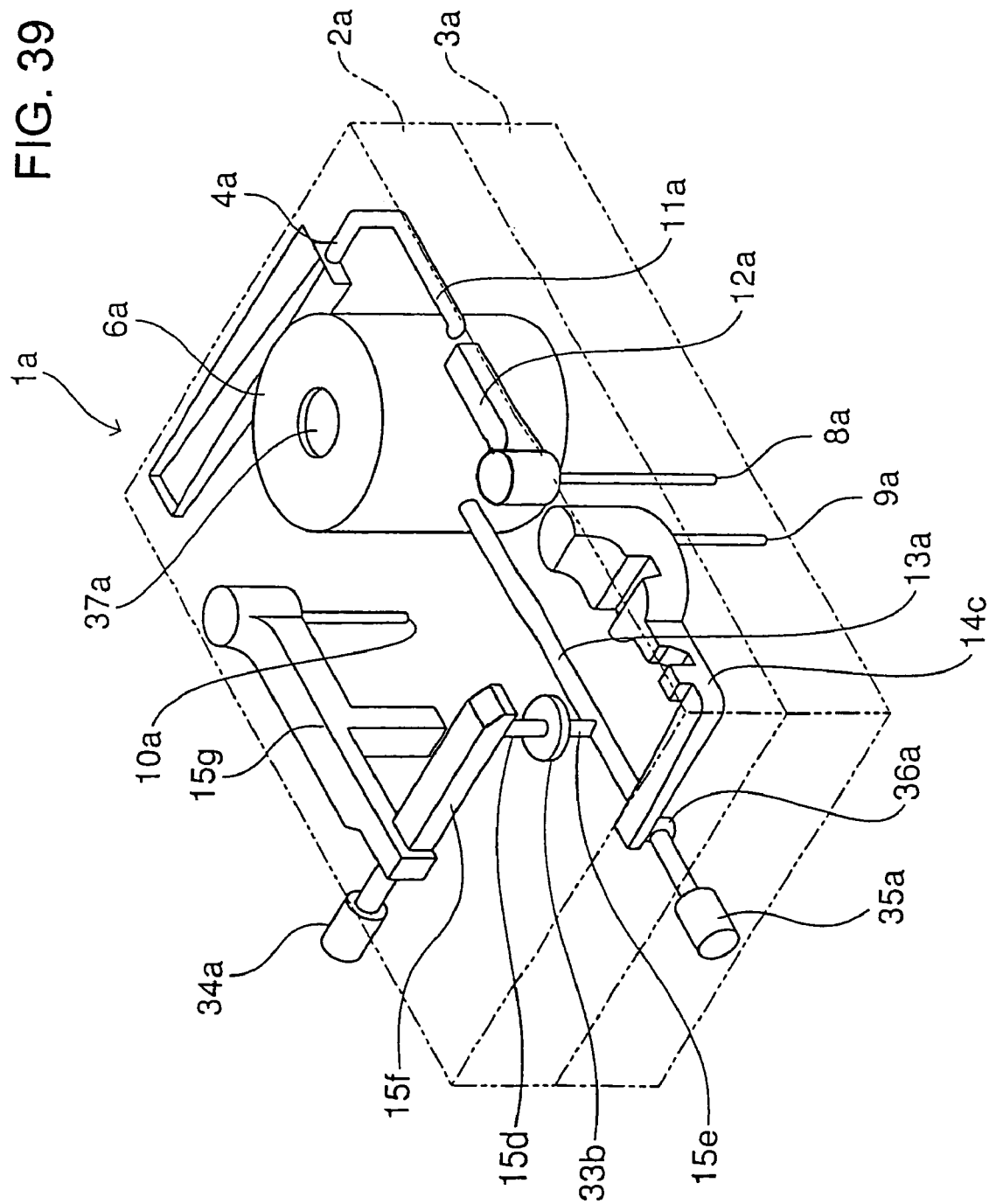
FIG. 39 is a perspective view illustrating the internal construction of the measuring unit according to the second embodiment.

FIGS. 37 and 38 are a top plan view and a front view of a measuring unit according to a second embodiment of the invention. FIG. 39 is a perspective view illustrating the internal construction of the measuring unit.

Figure 74:
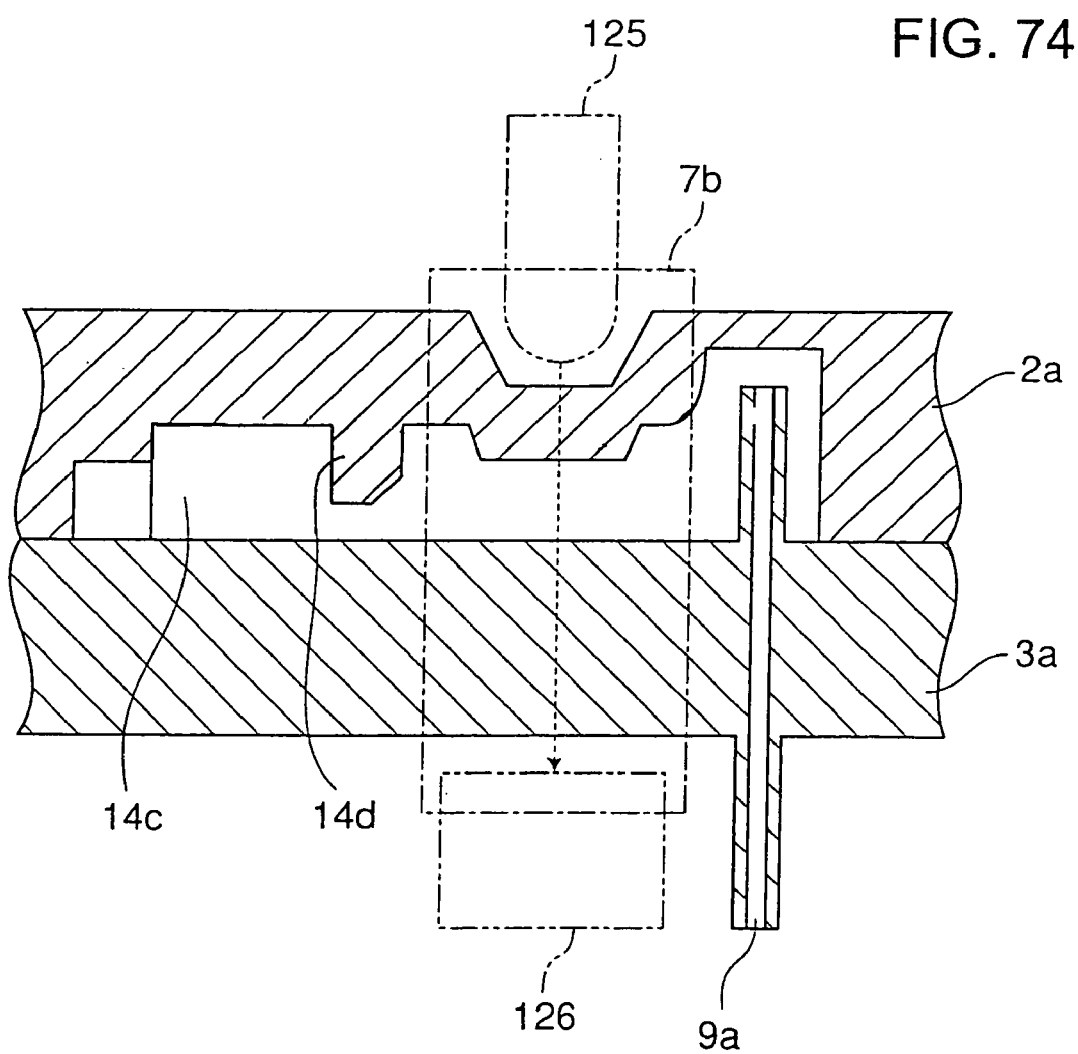
FIG. 74 is a sectional view illustrating a major portion of a channel of the measuring unit shown in FIG. 37.

As shown in FIGS. 37 to 39, a unit body 1a includes an upper plate 2a and a lower plate 3a composed of a transparent resin (e.g., an acryl resin or a polycarbonate resin containing an antistatic agent). The unit body 1a includes: an elongated sample receiving section 4a having a volume of 200 μL for receiving a sample; a rotary valve 6a including a diluent container 5a incorporated therein, and having a sample quantifying function and a flow path switching function; an electrical resistance measuring section 7a; an optical characteristic measuring section 7b; and first, second and third pump connection ports 8a, 9a and 10a. The connection ports 8a, 9a, 10a are each constituted by pipes projecting upward and downward from the lower plate 3a as shown in FIG. 74. The pipes of the connection ports 8a, 9a, 10a projecting downward are respectively inserted into pump connection tubes, while the pipes of the connection ports 8a, 9a, 10a projecting upward prevent liquid in channels 12a, 14c, 15g from being sucked out through the connection ports 8a, 9a, 10a.

Figure 73:
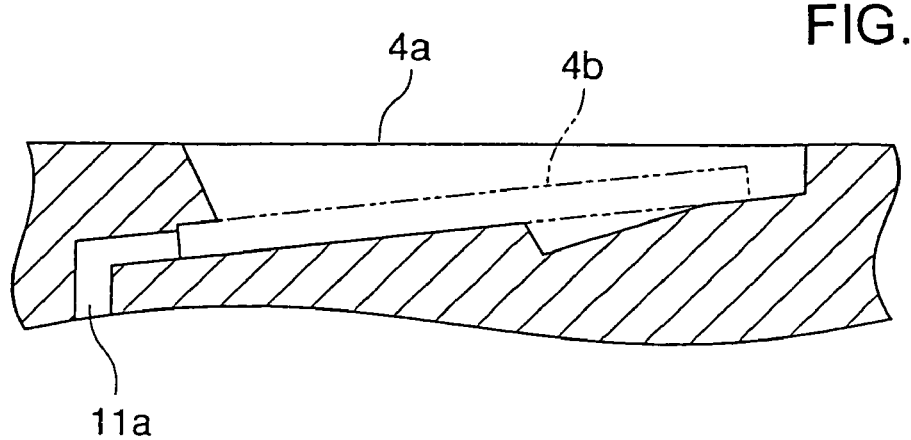
FIG. 73 is a sectional view illustrating a major portion of the measuring unit shown in FIG. 37.

The sample receiving section 4a has a sample injection port provided on the top thereof, and the bottom thereof is connected to the rotary valve 6a via a channel 11a. A capillary blood sampler 4b may be provided at the bottom of the sample receiving section 4a with a distal end thereof inserted in the channel 11a as shown in FIG. 73. The pump connection port 8a is connected to the rotary valve 6a via the channel 12a. The electrical resistance measuring section 7a and the optical characteristic measuring section 7b are connected to the rotary valve 6a via the channel 13a, to the pump connection port 9a via the channel 14c, and to the pump connection port 10a via the channel 15g.

As will be described later in detail, the channels 11a, 12a constitute a quantifying channel for introducing the sample to a sample quantifying section. The channel 13a constitutes a measuring channel for introducing a diluted sample from the diluent container 5a into the electrical resistance measuring section 7a and the optical characteristic measuring section 7b. Further, the channels 13a, 14c constitute an agitation channel for agitating a mixture of the quantified sample and a diluent for preparation of the diluted sample. The channel 15g allows the electrical resistance measuring section 7a to communicate with the pump connection port 10a to constitute a retention channel for retaining the diluted sample introduced therein after measurement.

As shown in FIGS. 39 and 74, the channel 14c is configured so that the sectional area thereof becomes greater toward the pump connection port 9a, and has a projection 14d provided on an interior surface thereof. With this arrangement, bubbles generated when the mixture of the quantified sample and the diluent is moved back and forth in arrow directions A and B for agitation thereof (to be described later with reference to FIG. 66) are prevented from flowing into the optical characteristic measuring section 7b (i.e., in the arrow direction A). Thus, occurrence of noises during measurement of an optical characteristic can be prevented.

2. Construction of Rotary Valve

Figure 40:
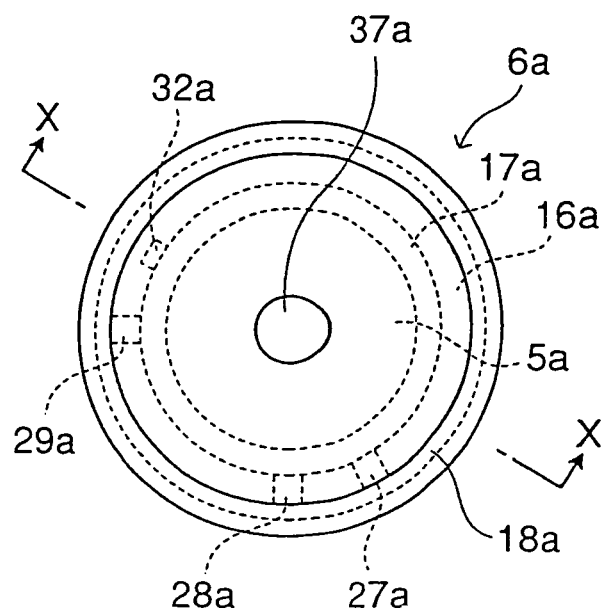
FIG. 40 is a top plan view of a rotary valve of the measuring unit according to the second embodiment.
Figure 41:
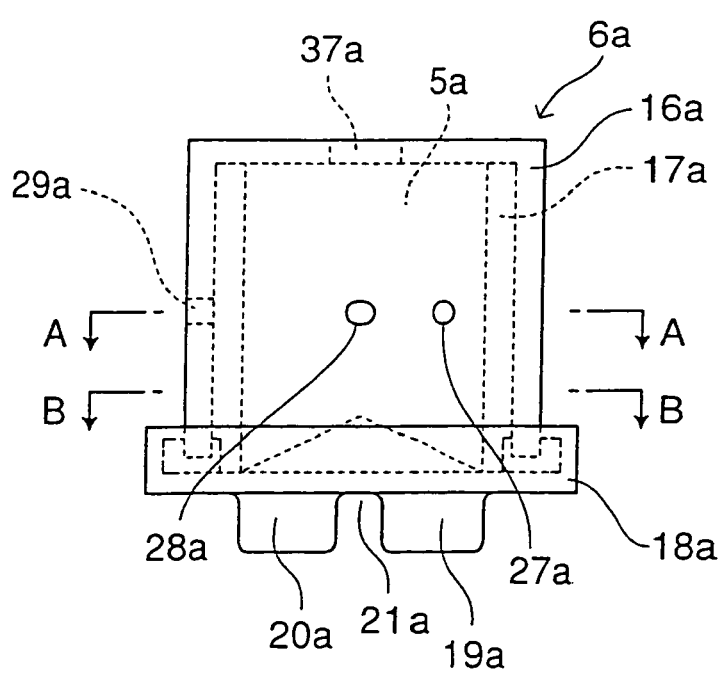
FIG. 41 is a front view of the rotary valve of the measuring unit according to the second embodiment.
Figure 42:
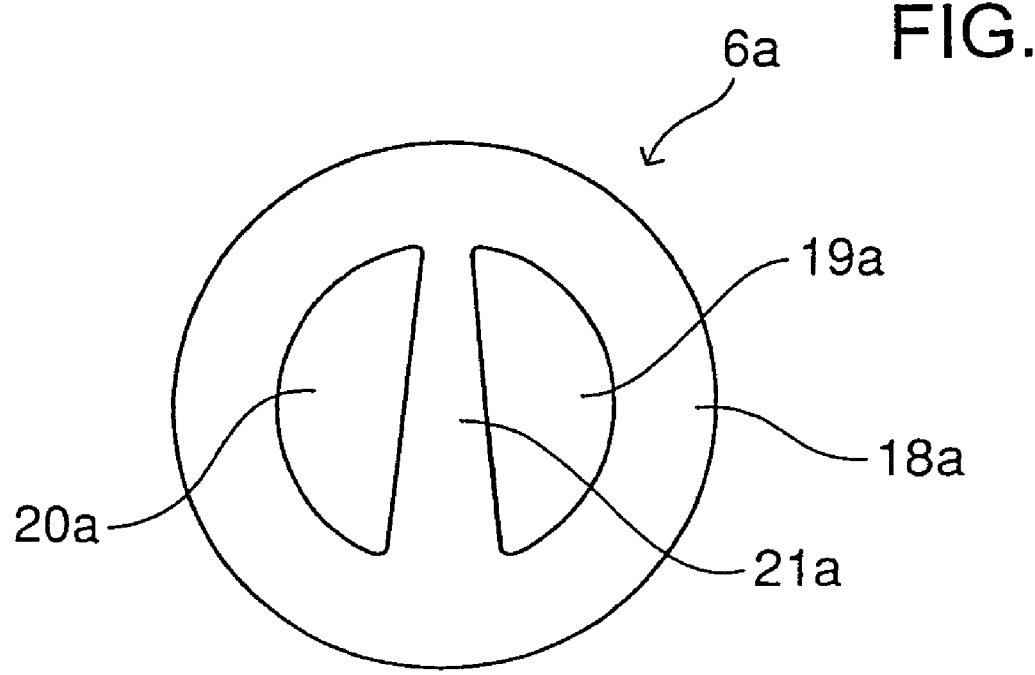
FIG. 42 is a bottom view of the rotary valve of the measuring unit according to the second embodiment.

FIGS. 40, 41 and 42 are a top plan view, a front view and a bottom view, respectively, of the rotary valve 6a. As shown in FIGS. 40 to 42, the rotary valve 6a includes an outer cylinder 16a having an open bottom, and an inner cylinder 17a having a closed bottom and inserted in the outer cylinder 16a from the bottom of the outer cylinder 16a. The inner cylinder 17a has an open top, and a flange 18a provided at the bottom thereof. The outer cylinder 16a has a through-hole 37a formed in the center of the top thereof for opening the diluent container 5a to the atmosphere. The through-hole 37a is usually closed by a sealing member not shown, and opened when the unit body 1a is used.

Projections 19a, 20a project downward from the flange 18a to define a groove 21a having non-parallel edges therebetween. The projections 19a, 20a constitute a connector to be connected to a valve driving source to be described later. When the inner cylinder 17a is rotated about an axis thereof, an outer circumferential surface of the inner cylinder 17a is slidable in contact with an inner circumferential surface of the outer cylinder 16a. Although the groove 21a has the non-parallel edges in this embodiment, the groove 21a may have parallel edges.

Figure 43:
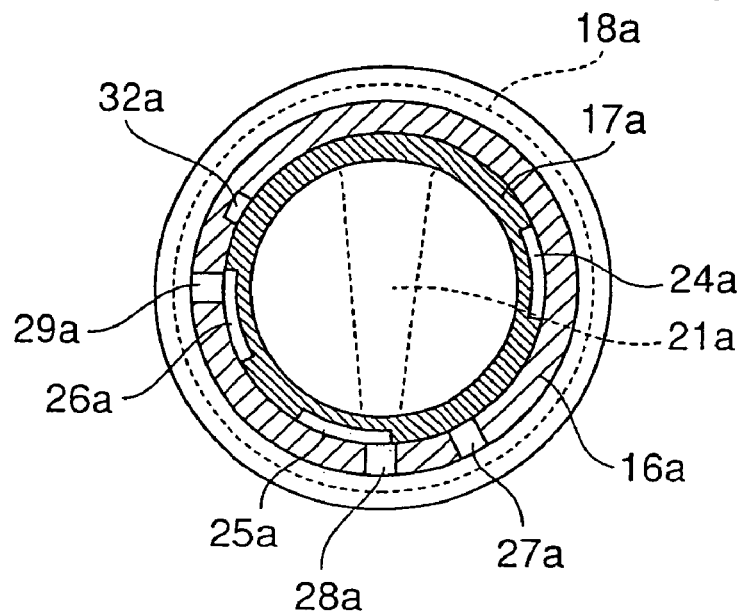
FIG. 43 is a sectional view of the rotary valve as seen from an arrow direction A-A in FIG. 41.
Figure 44:
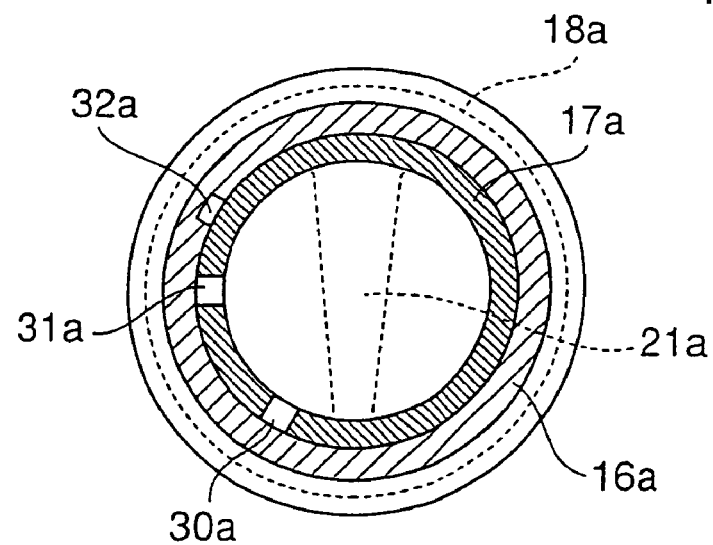
FIG. 44 is a sectional view of the rotary valve as seen from an arrow direction B-B in FIG. 41.
Figure 45:
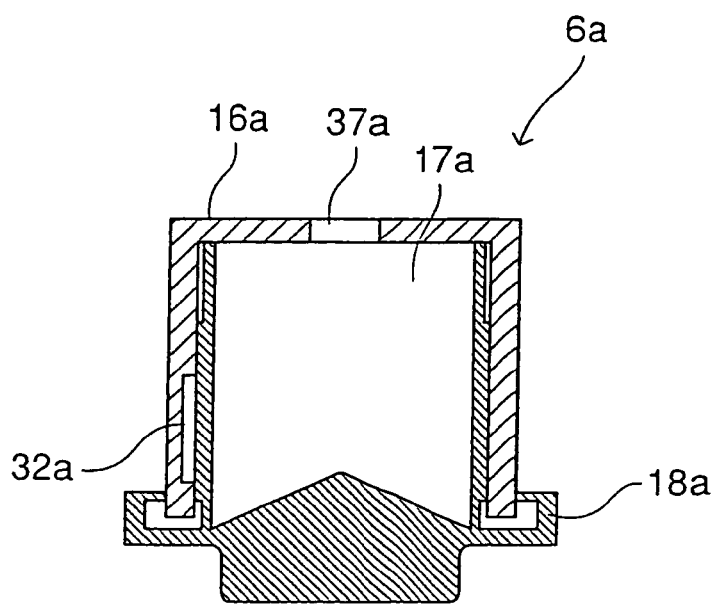
FIG. 45 is a sectional view of the rotary valve as seen from an arrow direction X-X in FIG. 40.

FIGS. 43 and 44 are sectional views of the rotary valve 6a as seen in arrow directions A-A and B-B, respectively, in FIG. 41. FIG. 45 is a sectional view of the rotary valve 6a as seen in an arrow direction X-X in FIG. 40.

As shown in FIG. 43, the inner cylinder 17a has three elongated lateral grooves 24a, 25a, 26a formed in circumferentially aligned relation in an upper portion of the outer circumferential surface thereof, and the outer cylinder 16a has three through-holes 27a, 28a and 29a communicating with the channels 11a, 12a and 13a, respectively.

As will be described later, the lateral groove 25a serves as the sample quantifying section, and the lateral grooves 24a, 26a serve as channel opening and closing grooves.

As shown in FIG. 44, the inner cylinder 17a has two through-holes 30a, 31a formed in a lower portion thereof for channel opening and closing. As shown in FIGS. 43 to 45, the outer cylinder 16a further has an elongated vertical groove 32a formed in the inner circumferential surface thereof as extending axially from an upper portion to a lower portion thereof.

Figure 47:
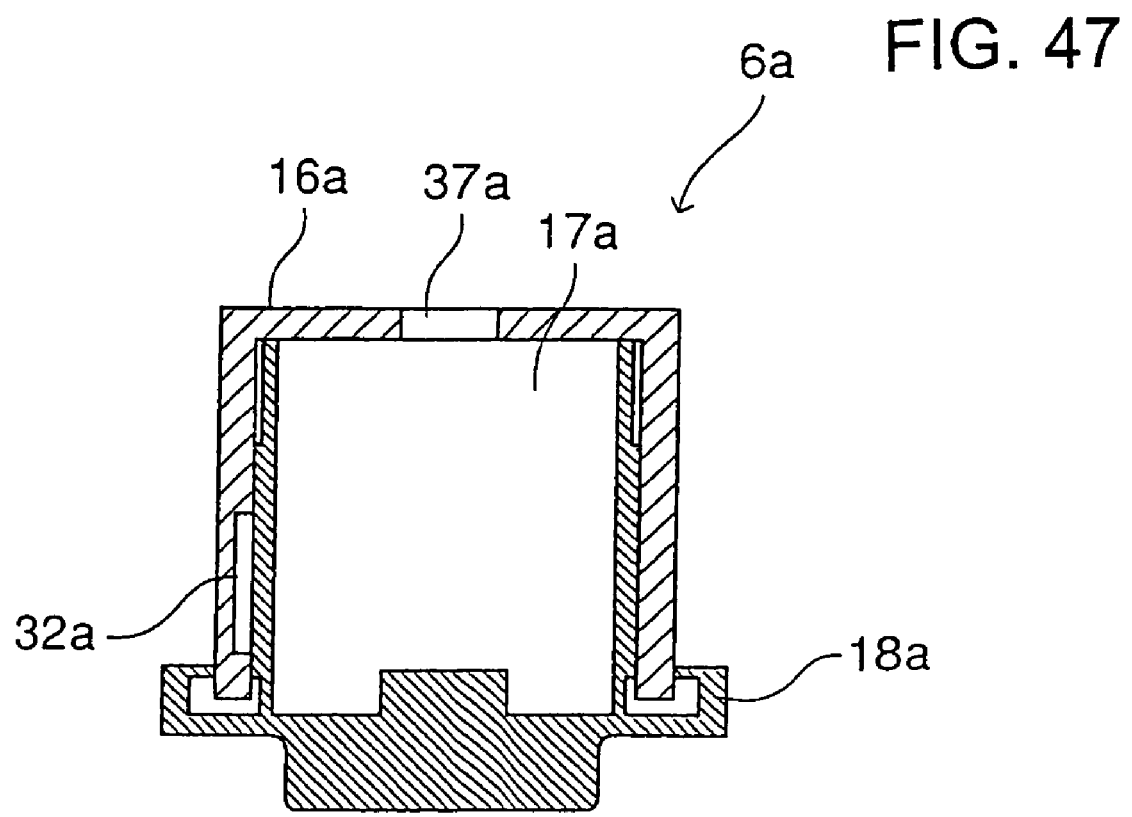
FIG. 47 is a sectional view illustrating a modification of the rotary valve.

As shown in FIG. 45, the inner cylinder 17a has an inwardly projecting conical bottom, which improves the efficiency of mixing the blood sample with the diluent in the inner cylinder 17a and makes it possible to completely discharge the sample. Alternatively, the inner cylinder 17a may have a cylindrical projection provided in the center portion of the bottom thereof as shown in FIG. 47. As shown in FIGS. 45 and 47, the outer peripheral edge of the flange 18a projects upward in a ring shape. With this arrangement, liquid which happens to leak through the side face of the inner cylinder 17a is retained in the flange 18a. A gap is defined between parts of the outer cylinder 16a and the inner cylinder 17a. This alleviates a load exerted on a stepping motor 105a during the rotation of the inner cylinder 17a.

3. Construction of Electrical Resistance Measuring Section

As shown in FIGS. 37 and 39, the electrical resistance measuring section 7a includes a disk pellet (separation plate) 33b provided between vertical portions 15d and 15e of an internal channel 15f thereof, an electrode 34a provided in a junction between the channels 15g and 15f with an end thereof exposed to the inside of the channel and the other end thereof exposed to the outside of the upper plate 2a, and an electrode 35a provided in a junction 36a between the channels 13a and 14c with an end thereof exposed to the inside of the channel and the other end thereof exposed to the outside of the lower plate 3a.

Figure 46:
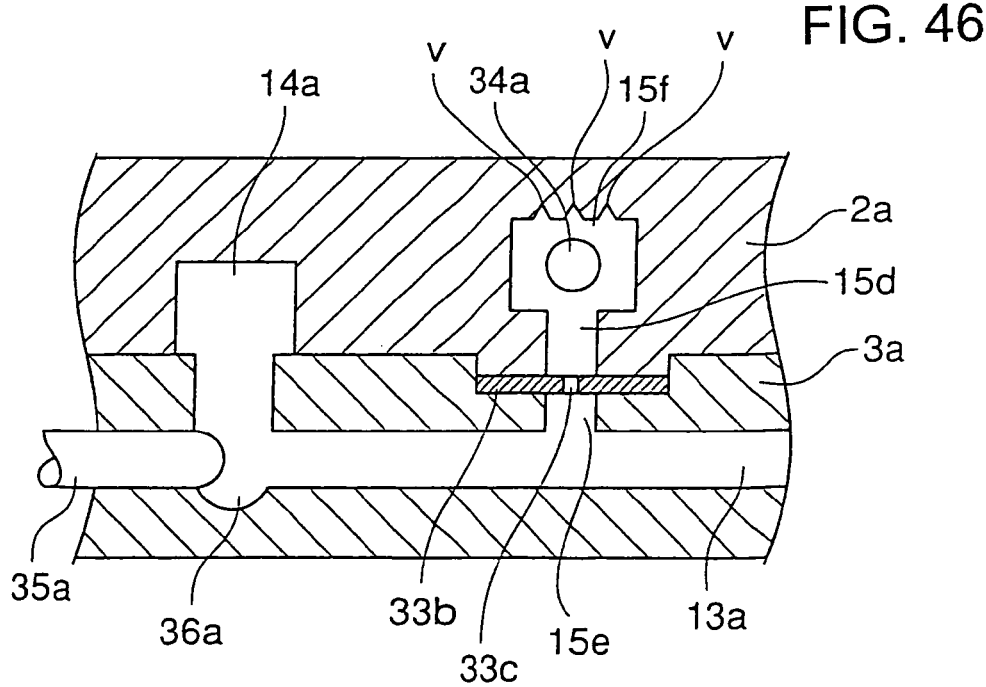
FIG. 46 is a sectional view illustrating a major portion of an electrical resistance measuring section of the measuring unit according to the second embodiment.

FIG. 46 is a sectional view illustrating a major portion of the electrical resistance measuring section 7a. The pellet 33b is fitted in a round recess formed in the lower plate 3a coaxially with the vertical portion 15e and pressed by a round projection provided on the upper plate 2a coaxially with the vertical portion 15d.

The pellet 33b has a minute through-hole 33c formed in the center thereof, so that the electrical resistance of an electrolytic solution passing through the minute through-hole 33c is measured by the electrodes 34a, 35a. The pellet 33b is formed of a polyetherimide sheet having a thickness of 125 µm. The minute through-hole 33c is formed in the sheet as having a diameter of 100 µm by an excimer laser.

As shown in FIG. 46, a plurality of grooves V are formed in an upper wall surface (ceiling surface) of the channel 15f as extending parallel to each other longitudinally of the channel 15f. With this arrangement, bubbles in the electrolytic solution flowing through the minute through-hole 33c in the channel 15f are trapped by the grooves V, and the electrolytic solution is rectified for stabilization of the flow thereof. This suppresses noises in measurements obtained by means of the electrodes 34a, 35a.

4. Construction of Optical Characteristic Measuring Section

As shown in FIG. 37, the optical characteristic measuring section 7b is located in the vicinity of the pump connection port 9a of the channel 14c. In the optical characteristic measuring section 7b, the channel 14c is configured so that a light emitting diode 125 and a photodiode 126 of the analyzer (to be described later) can be provided on upper and lower sides of the channel 14c as shown in FIG. 74 for measurement of the intensity of light transmitted through liquid present in the channel 14c.

5. Analyzer

Figure 48:
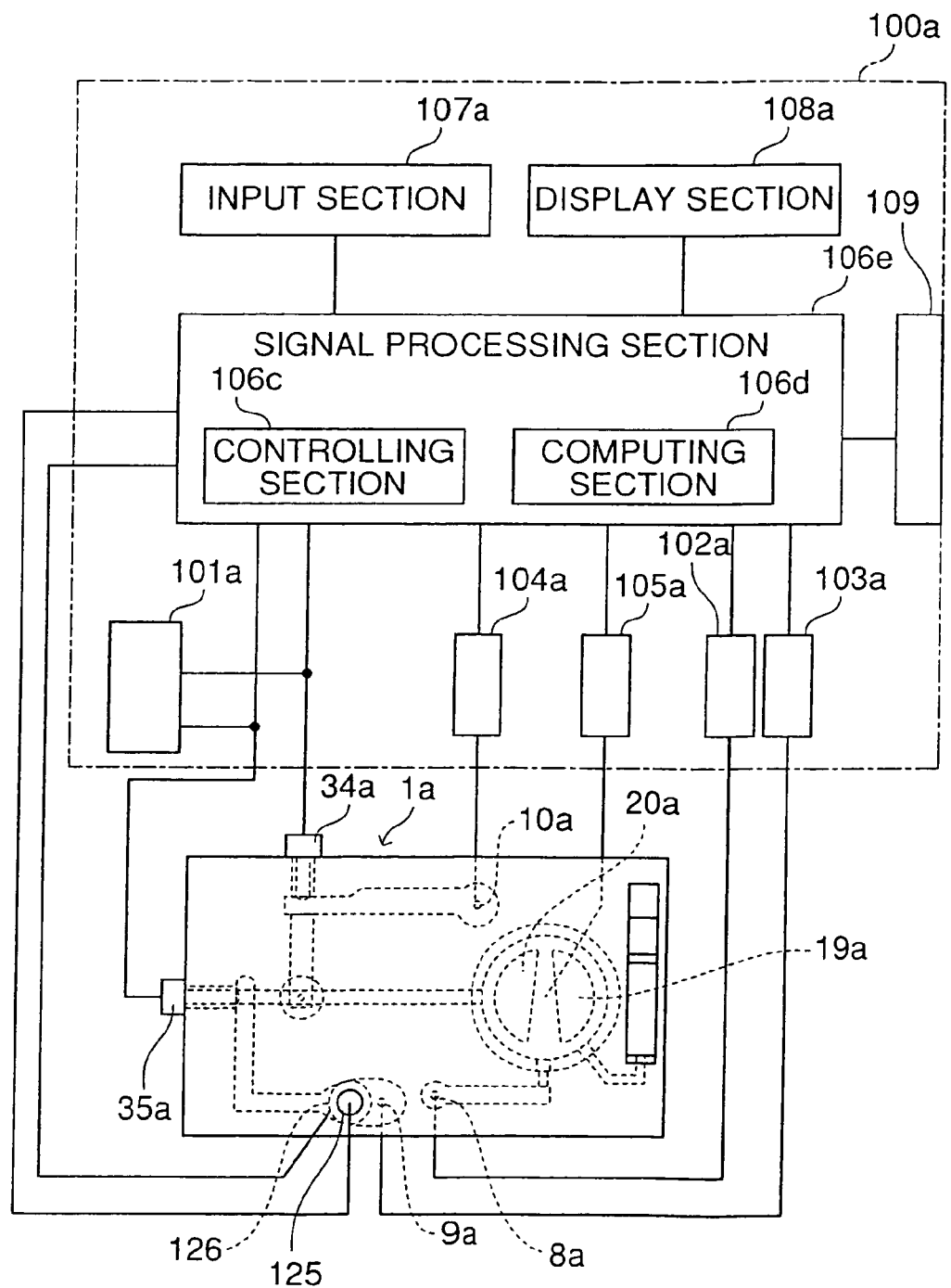
FIG. 48 is a block diagram illustrating the construction of an analyzer according to the second embodiment.

FIG. 48 is a block diagram illustrating the construction of an analyzer 100a which analyzes white blood cells and hemoglobin in a blood sample with the use of the unit body 1a. A constant direct current source 101a of the analyzer 100 is detachably connected to the exposed ends of the electrodes 34a, 35a of the unit body 1a, and electric syringe pumps 102a, 103a and 104a are detachably connected to the first, second and third pump connection ports 8a, 9a and 10a, respectively. A stepping motor 105a for driving the valve 6a is detachably connected to the valve 6a via a connector (not shown) engaged with the groove 21a formed in the flange 18a at the bottom of the valve 6a.

A signal processing section 106e includes a controlling section 106c and a computing section 106d, which are comprised of a microprocessor. The controlling section 106c drives the electric syringe pumps 102a, 103a, 104a, the stepping motor 105a and the light emitting diode 125 in response of a command applied thereto from an input section 107a. The computing section 106d counts the number of the white blood cells and calculates the size of each of the white blood cells on the basis of signals applied from the electrodes 34a, 35a. Further, the computing section 106d calculates the amount of the hemoglobin on the basis of signals from the photodiode 126. The results of the calculations are displayed on a display section 108a.

The analyzer 100a further includes an input/output port (interface) 109 for interfacing the signal processing section 106e with an external computer and printer for signal reception and transmission.

6. Measuring Operation

Figure 49:
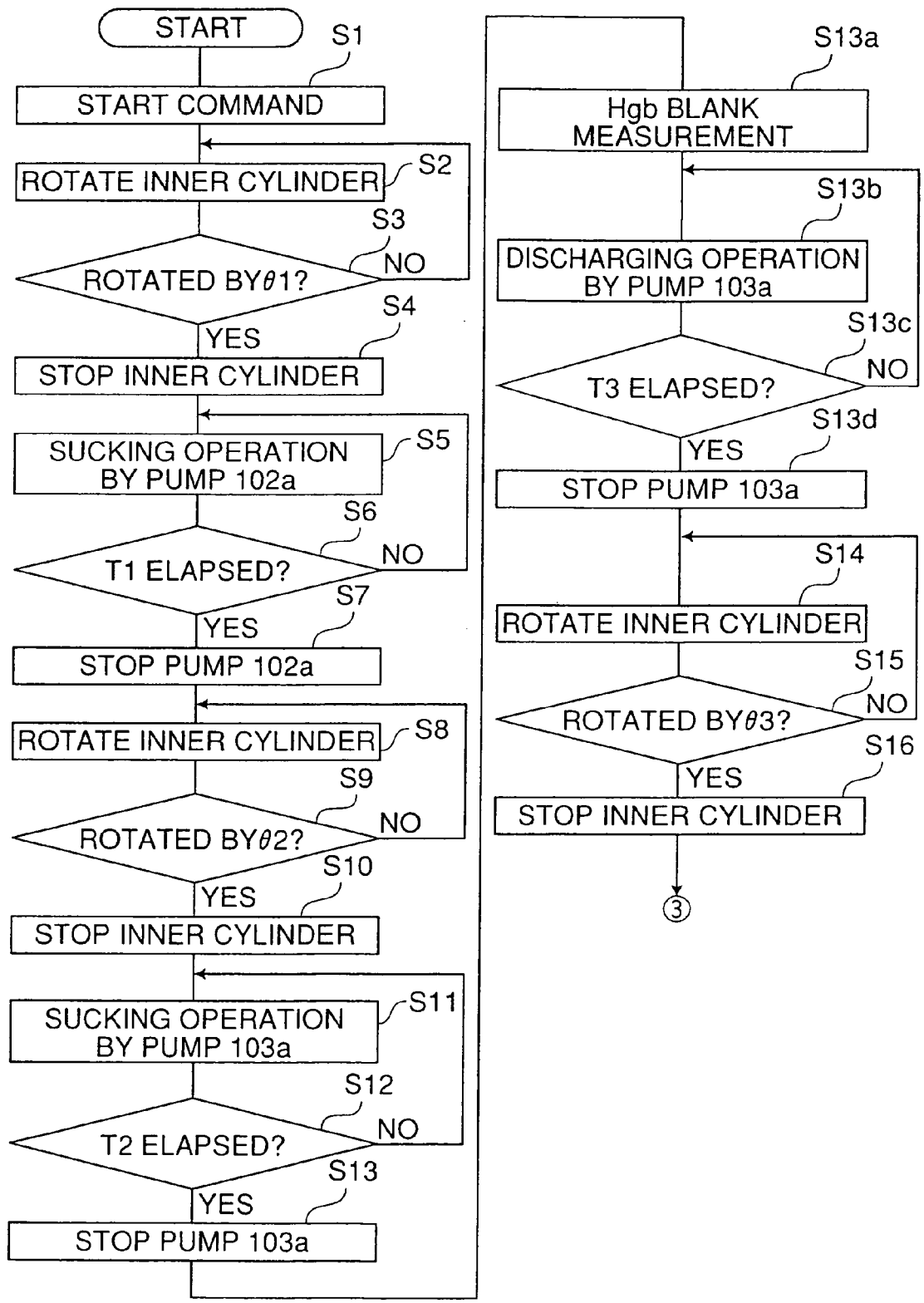
FIGS. 49 to 51 are flow charts for explaining the operation of the analyzer according to the second embodiment.
Figure 50:
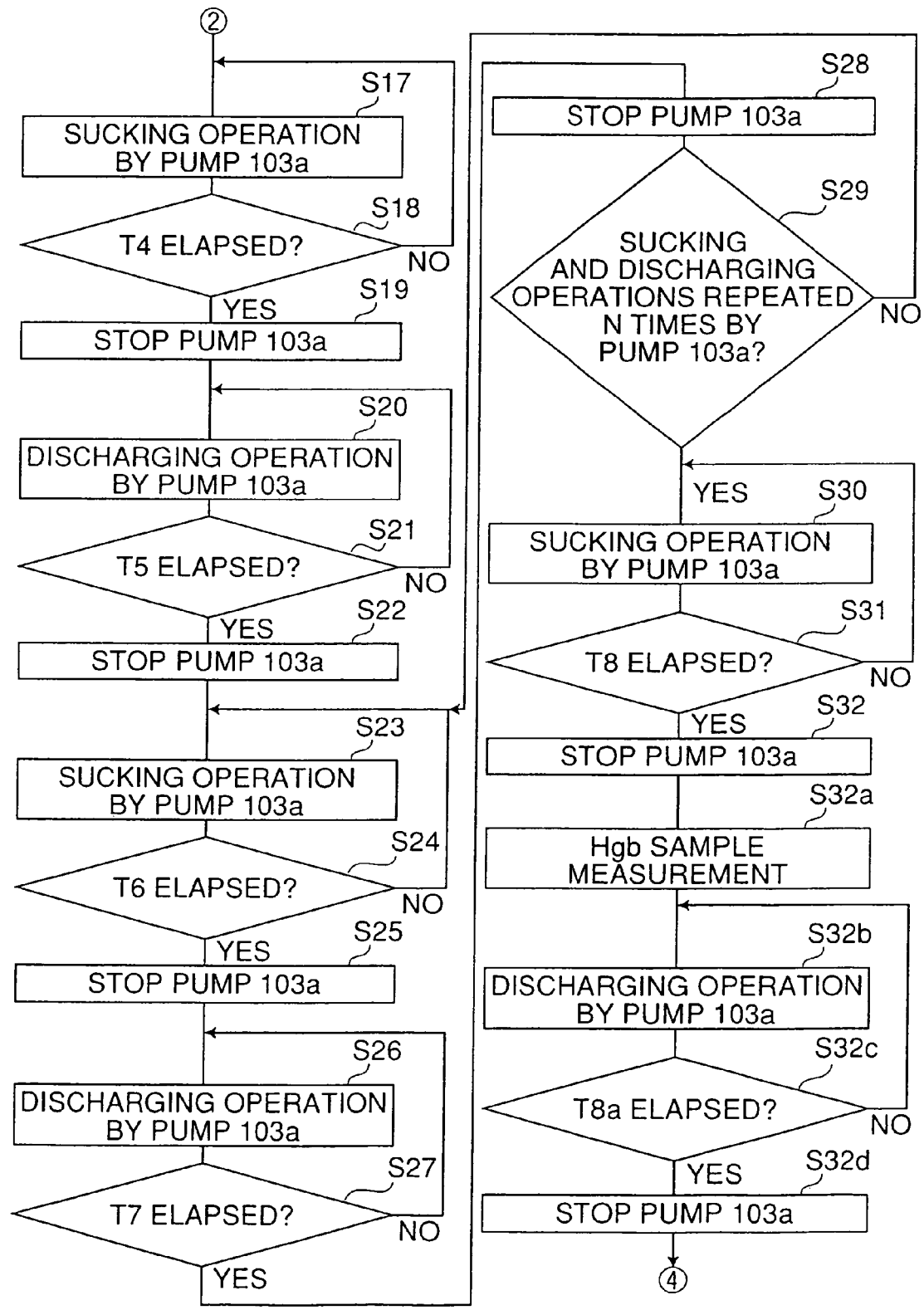
Figure 51:
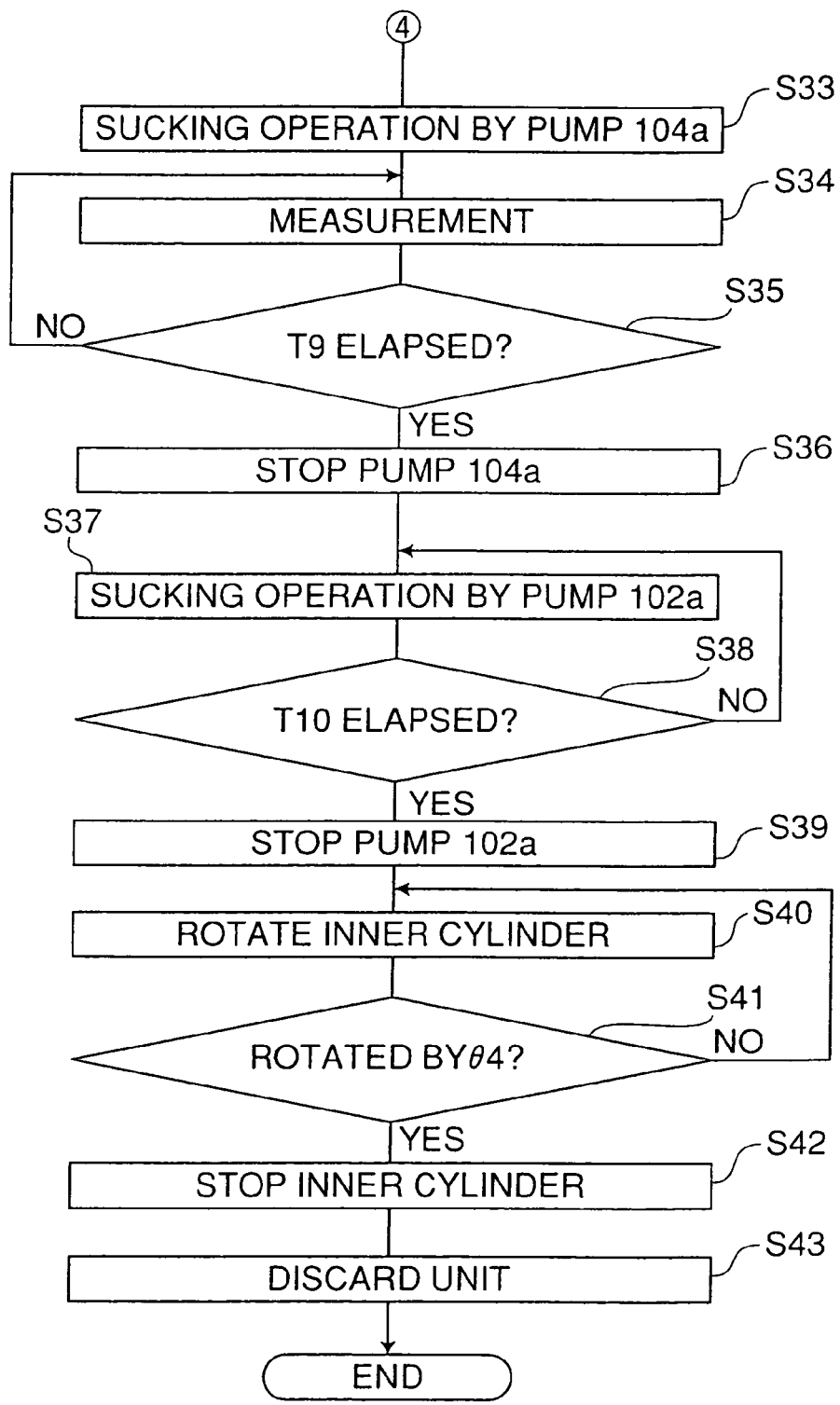

With reference to flow charts shown in FIGS. 49 to 51, an explanation will hereinafter be given to the operation of the analyzer 100a shown in FIG. 48. FIGS. 52(a), 52(b), 53(a), 53(b), 54(a), 54(b), 55(a), 55(b), 56(a) and 56(b) illustrate rotational positions of the inner cylinder 17a with respect to the outer cylinder 16a of the rotary valve 6a. Particularly, FIGS. 52(a) to 56(a) and FIGS. 52(b) to 56(b) are sectional views of the rotary valve 6a as seen in arrow directions A-A and B-B, respectively, in FIG. 41.

In the unit body 1a, the rotary valve 6a retains 1,000 μL of the diluent (a mixture of a dilution agent and a hemolyzing agent) preliminarily quantified in the diluent container 5a. The inner cylinder 17a is initially in a rotational position as shown in FIGS. 52(a) and 52(b) with respect to the outer cylinder 16a, so that the diluent L is confined in the container 5a as shown in FIG. 57.

Figure 57:
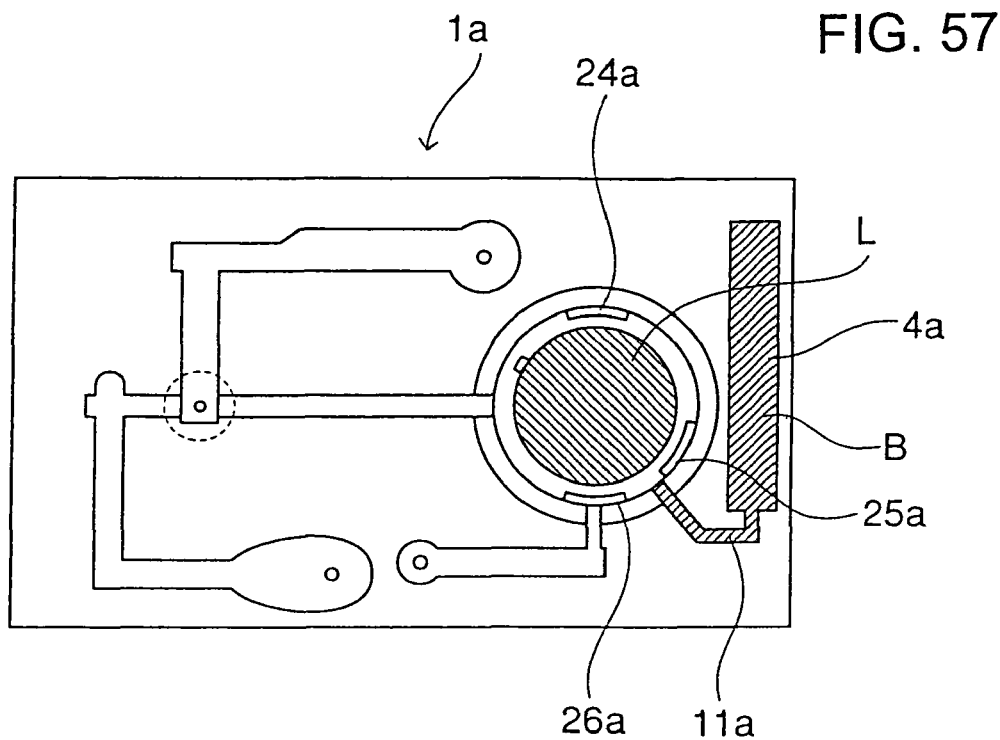
FIGS. 57 to 72 are diagrams for explaining the movement of a sample and a diluent in the measuring unit according to the second embodiment.

The unit body 1a is connected to the analyzer 100a as shown in FIG. 48, and about 10 μL to about 150 μL of a whole blood sample B is injected into the sample receiving section 4a by a syringe or a pipette as shown in FIG. 57. Alternatively, the capillary blood sampler in which the whole blood sample is retained may be inserted into an inlet of the channel 11a. Then, the sealing member on the top of the outer cylinder 16a of the rotary valve 6a is removed to open the through-hole 37a. The sealing member may be removed by a user of the analyzer 100a or, alternatively, the sealing member may be pierced by a piercing needle which may be provided in the analyzer 100a.

Figure 52A:
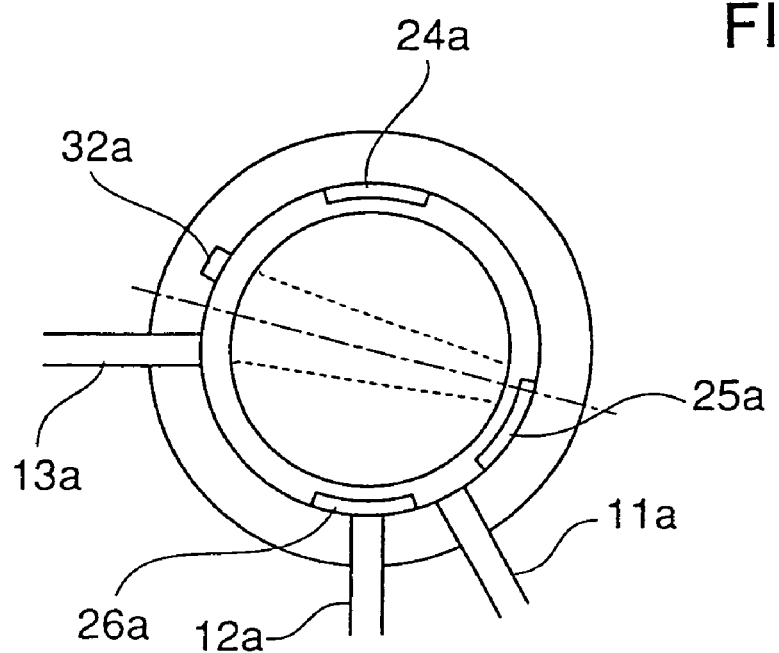
FIGS. 52(a) and 52(b) are diagrams for explaining the operation of the rotary valve of the measuring unit according to the second embodiment.
Figure 52B:
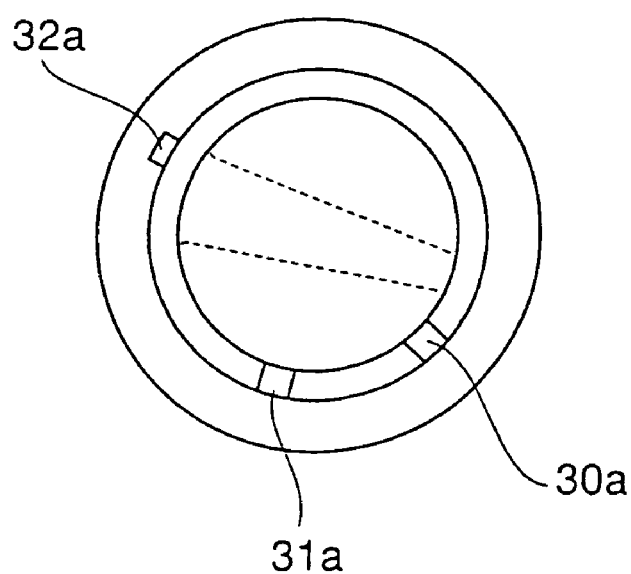
Figure 53A:
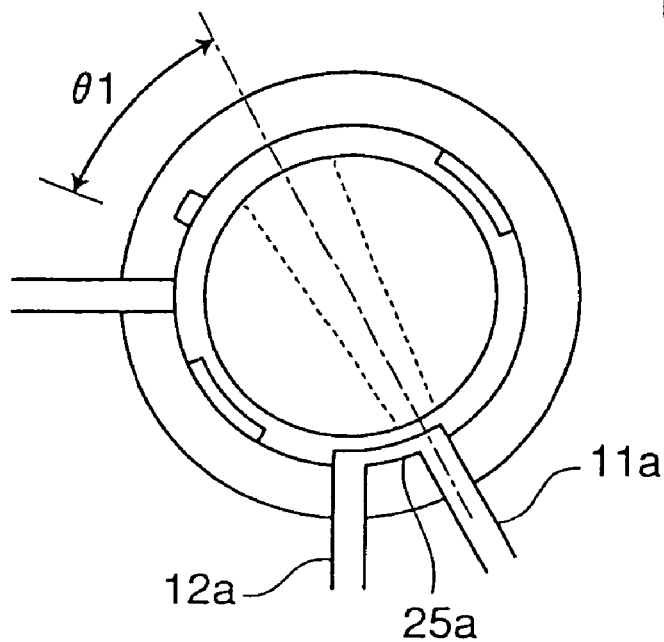
FIGS. 53(a) and 53(b) are diagrams for explaining the operation of the rotary valve of the measuring unit according to the second embodiment.
Figure 53B:
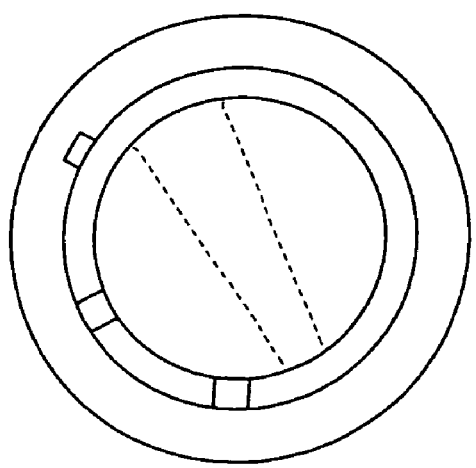
Figure 58:
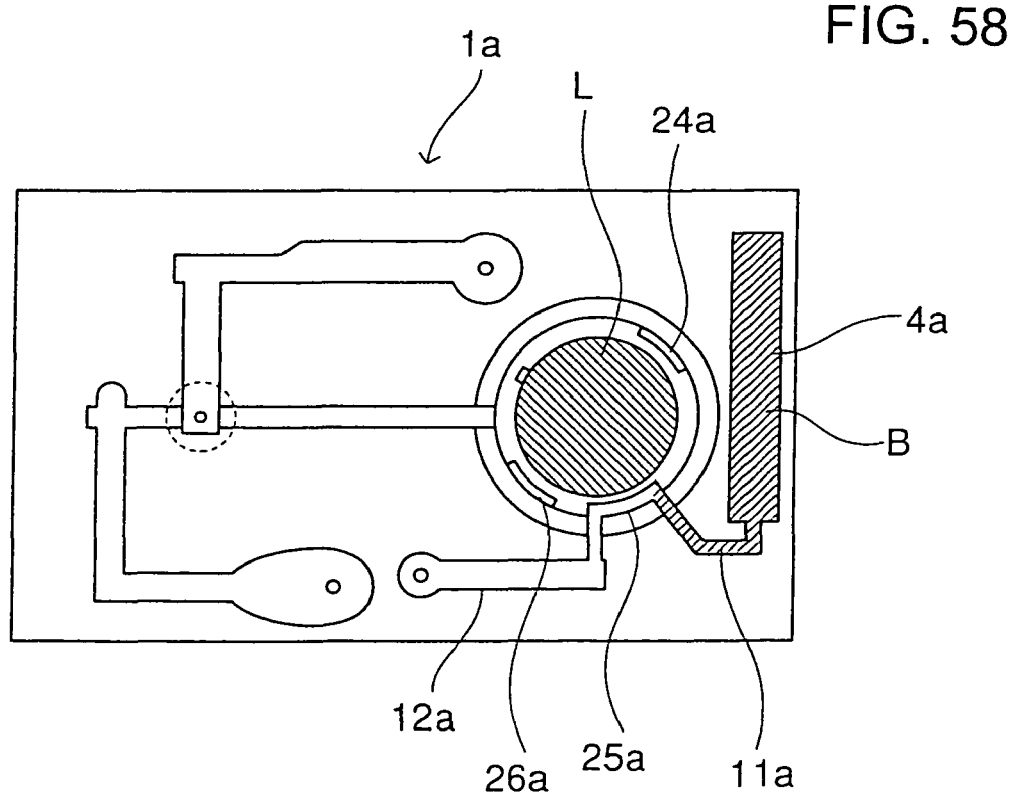

When a start command is applied from the input section 107a (FIG. 48) (Step S1), the stepping motor 105a is driven so that the inner cylinder 17a is rotated clockwise by an angle θ1 from the position shown in FIG. 52(a) and 52(b) (Steps S2 to S4) thereby to reach a position as shown in FIGS. 53(a), 53(b) and 58.

Figure 59:
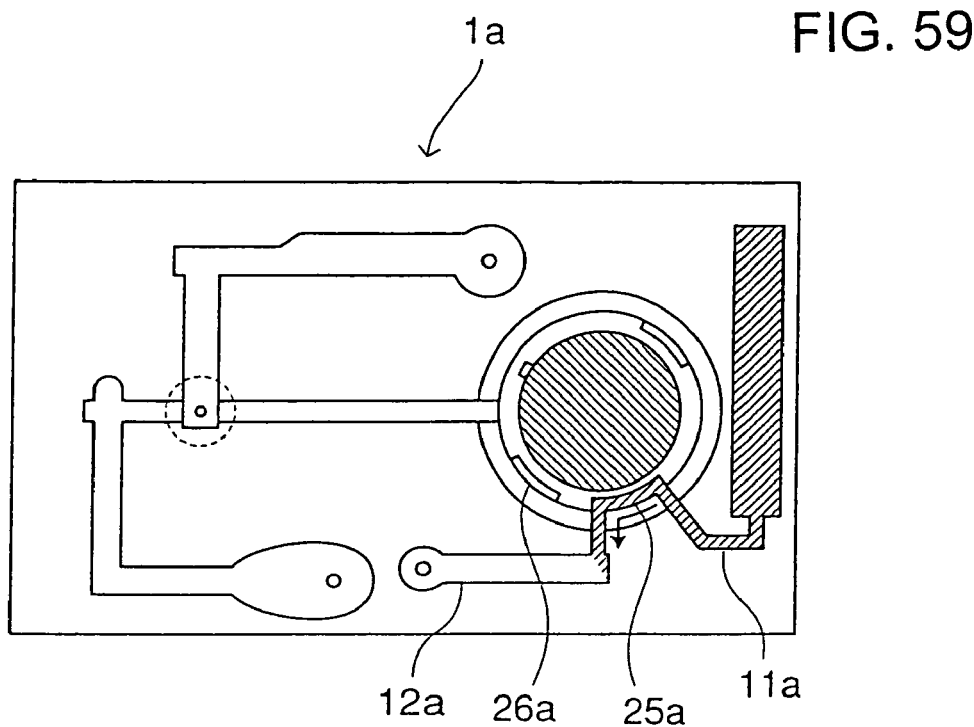

Thus, the channels 11a, 12a communicate with each other via the lateral groove 25a to form the quantifying channel as shown in FIGS. 53(a) and 58. In this state, the syringe pump 102a performs a sucking operation for a time period T1 (Step S5 to S7), whereby the sample B flows into the channel 12a from the sample receiving section 4a via the lateral groove 25a to fill the lateral groove 25a as shown in FIG. 59.

Figure 54A:
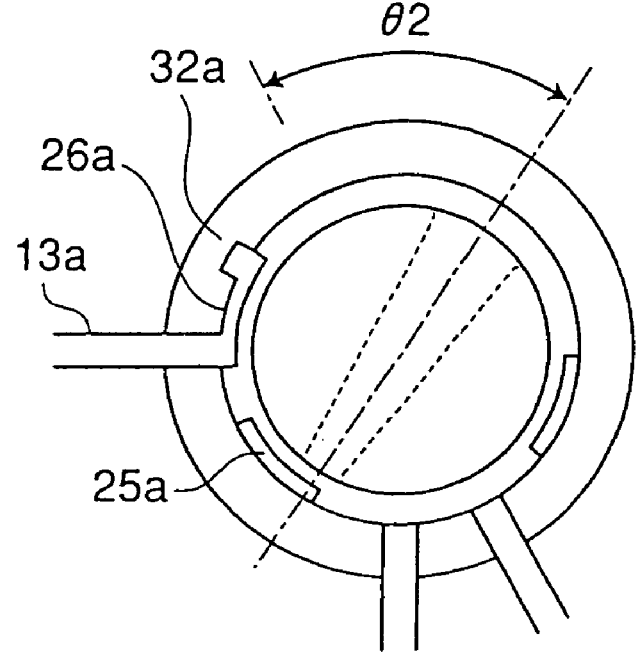
FIGS. 54(a) and 54(b) are diagrams for explaining the operation of the rotary valve of the measuring unit according to the second embodiment.
Figure 54B:
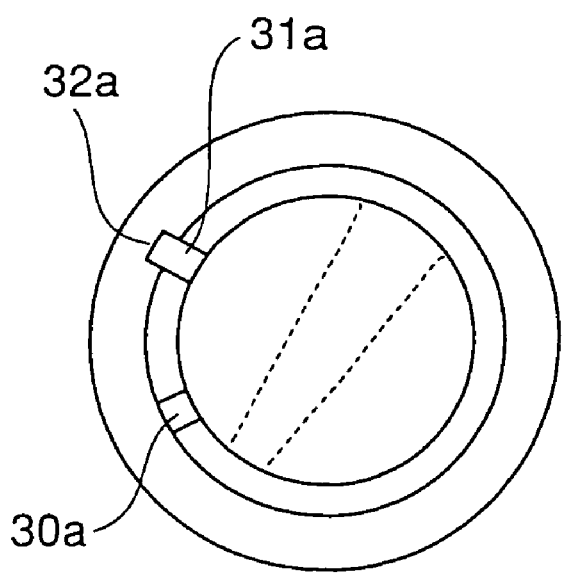
Figure 60:
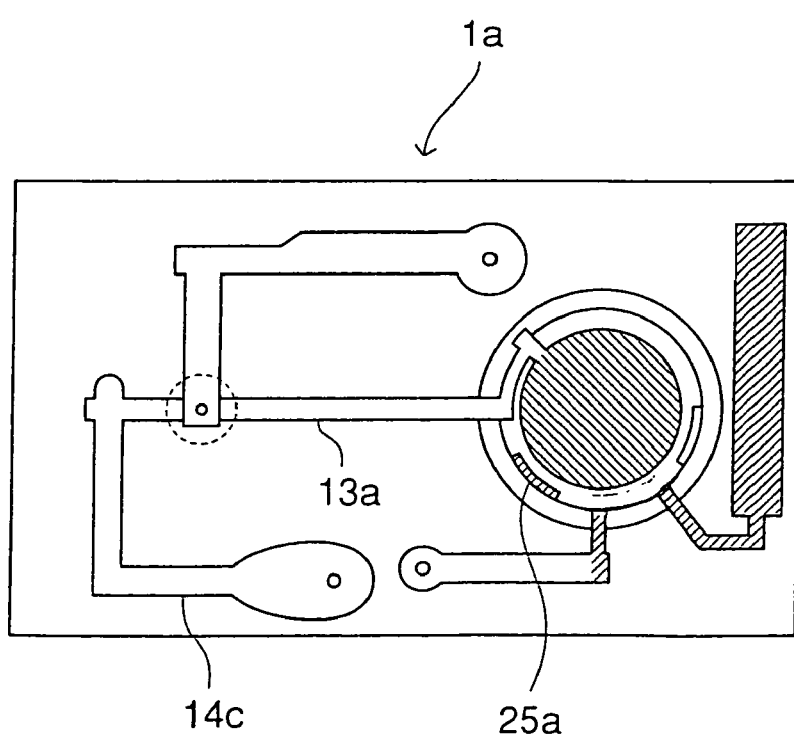

In turn, the stepping motor 105a is driven so that the inner cylinder 17a is rotated clockwise by an angle θ2 (Steps S8 to S10) thereby to reach a position as shown in FIGS. 54(a), 54(b) and 60. Thus, the sample is quantified in a volume of 2 μm which is equivalent to the volume of the lateral groove 25a, and separated by the inner circumferential surface of the outer cylinder 16a as shown in FIG. 60.

At the same time, the channel 13a communicates with the bottom of the diluent container 5a via the lateral groove 26a, the vertical groove 32a and the through-hole 31a as shown in FIGS. 54(a) and 54(b).

Figure 61:
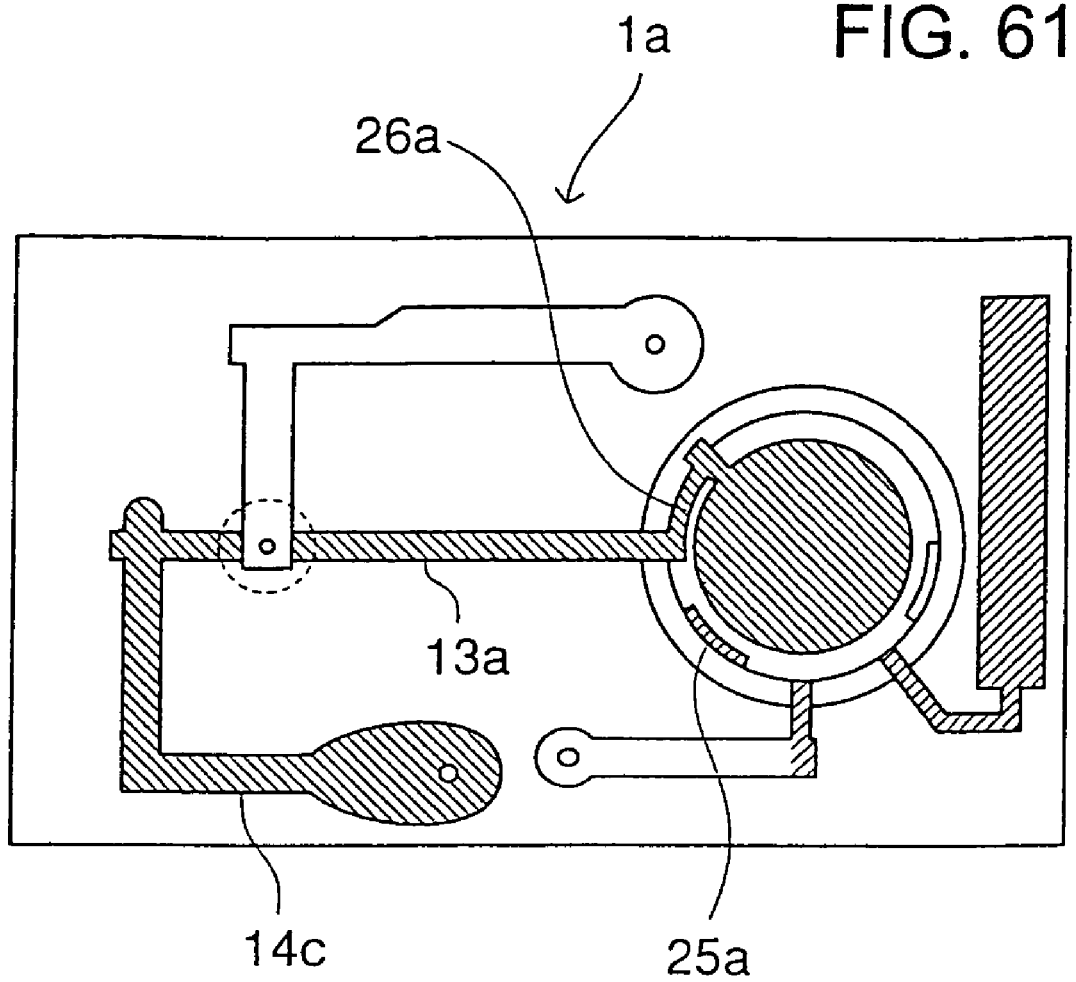
Figure 62:
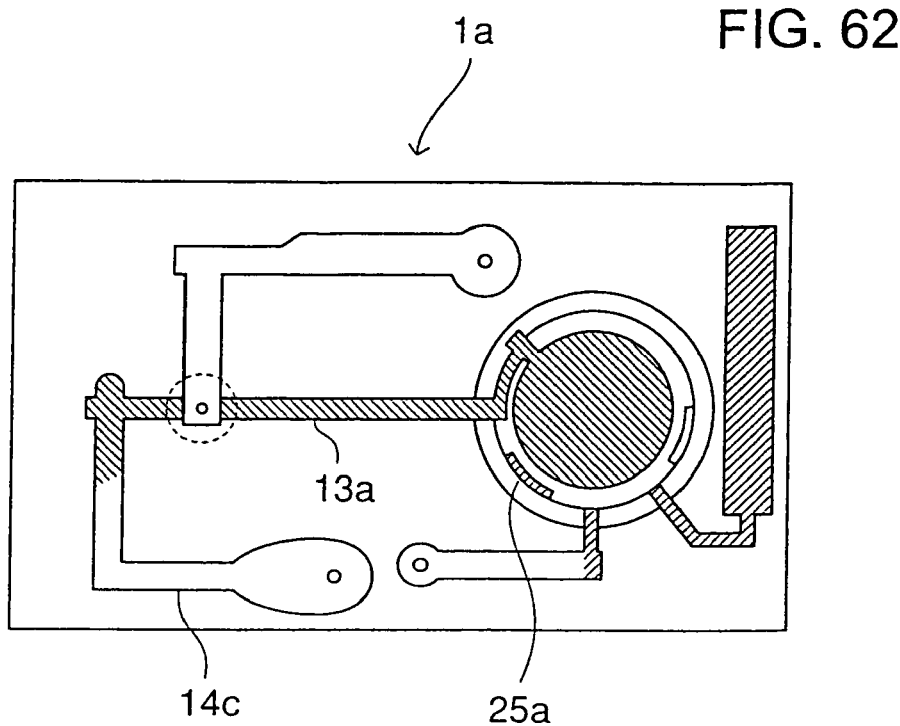

Then, the syringe pump 103a performs a sucking operation for a time period T2 (Steps S11 to S13), whereby the diluent L is introduced into the channels 13a, 14c from the diluent container 5a as shown in FIG. 61. In this state, the light emitting diode 125 is actuated, and the photodiode 126 measures the intensity of the light transmitted through the diluent (blank level) (Step S13a). When the syringe pump 103a performs a discharging operation for a time period T3 (Steps S13b to 13d), the diluent L is fed back into the diluent container 5a as shown in FIG. 62.

Figure 55A:
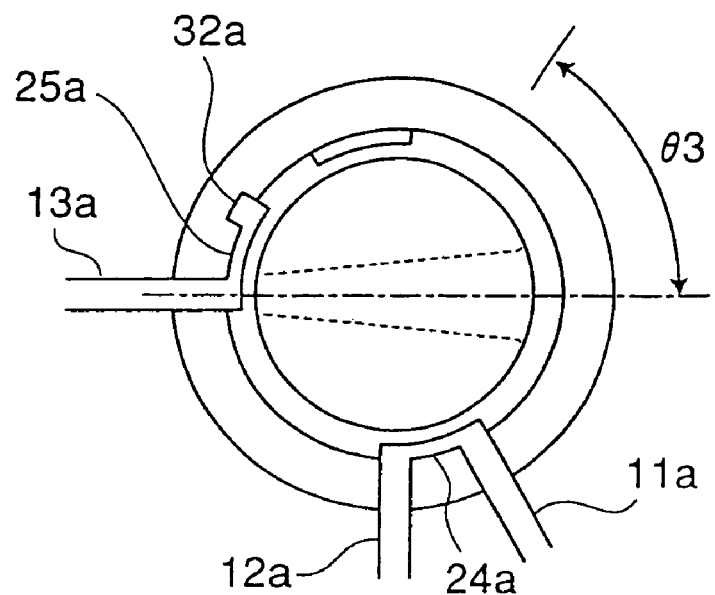
FIGS. 55(a) and 55(b) are diagrams for explaining the operation of the rotary valve of the measuring unit according to the second embodiment.
Figure 55B:
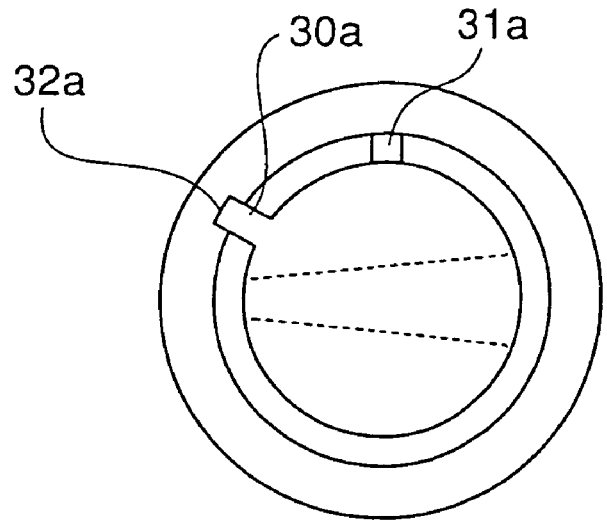

Subsequently, the stepping motor 105a is driven so that the inner cylinder 17a is rotated by an angle θ3 (Steps S14 to 16) thereby to reach a position as shown in FIGS. 55(a) and 55(b).

Figure 63:
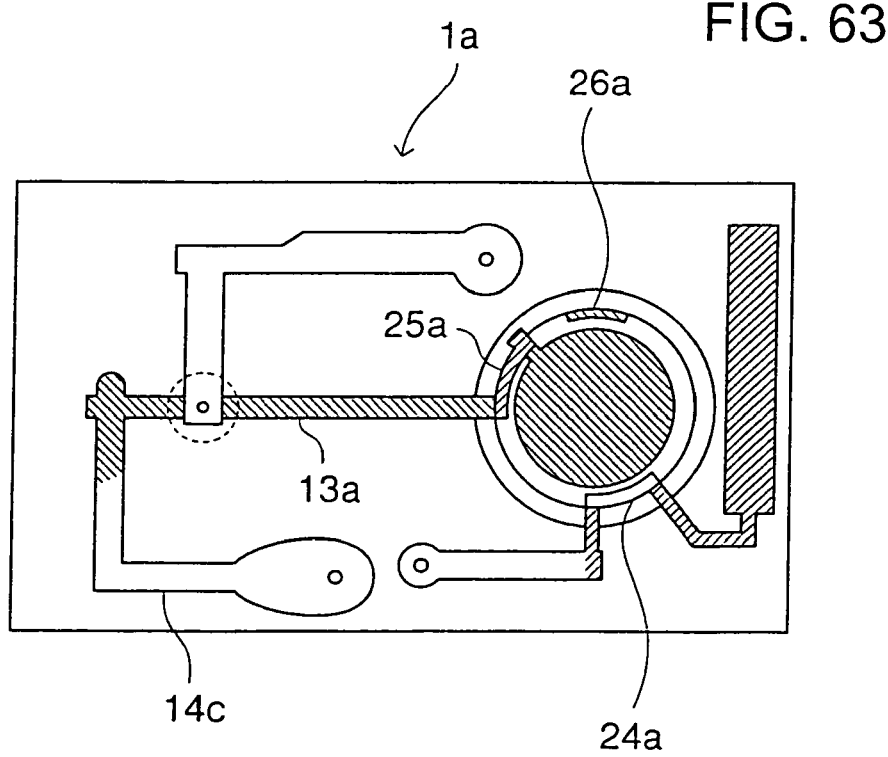

Thus, the channel 13a communicates with the bottom of the diluent container 5a via the lateral groove 25a, the vertical groove 32a and the through-hole 30a to form the agitation channel as shown in FIGS. 55(a), 55(b) and 63. At the same time, the channel 11a communicates with the channel 12a via the lateral groove 24a as shown in FIG. 55(a).

Figure 64:
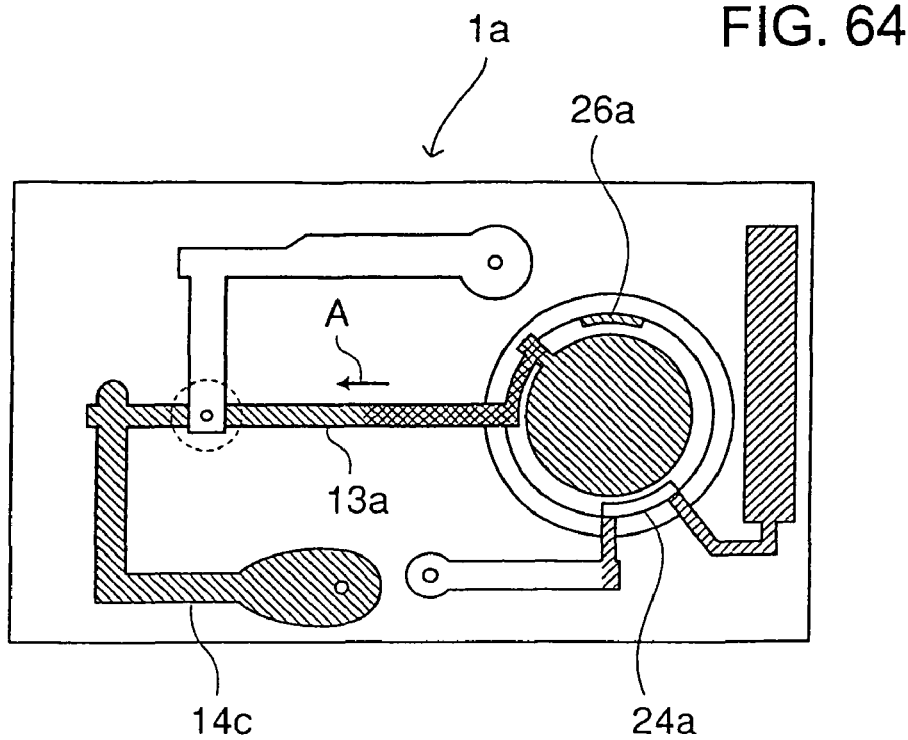

Then, the syringe pump 103a further performs the sucking operation for a time period T4 (Steps S17 to S19), whereby the diluent L in the diluent container 5a and the quantified sample in the lateral groove 25a are introduced into the channel 13a as shown in FIG. 64.

Figure 65:
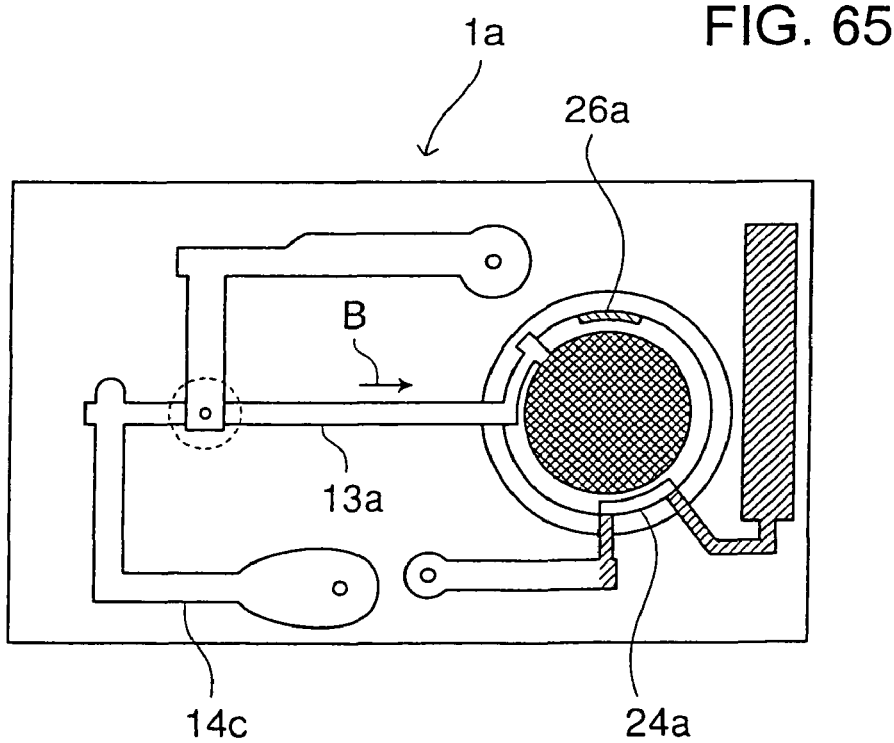

In turn, the syringe pump 103a performs a discharging operation for a time period T5 (Steps S20 to S22), whereby the sample and the diluent are fed back into the diluent container 5a as shown in FIG. 65.

Figure 66:
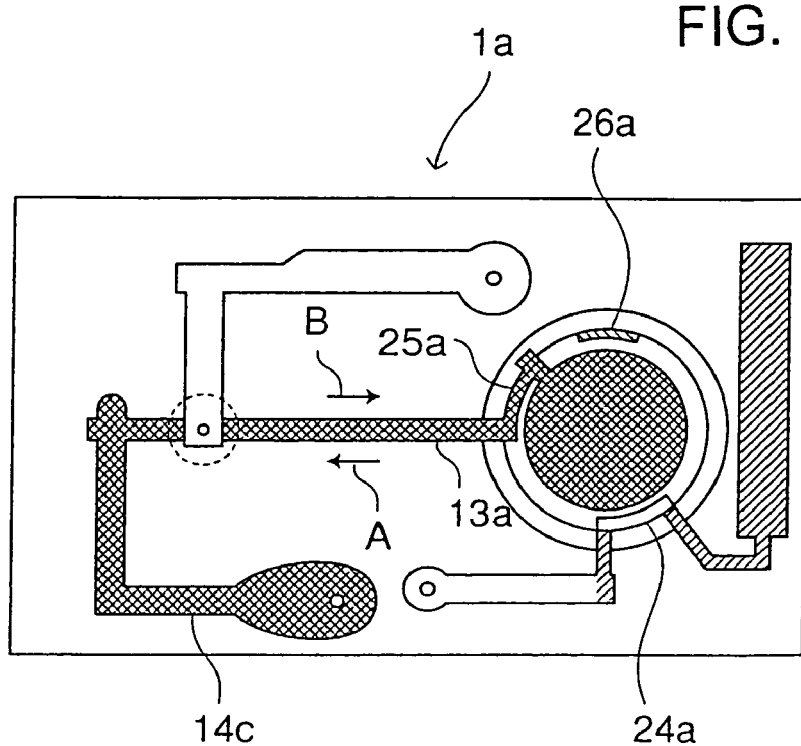
Figure 67:
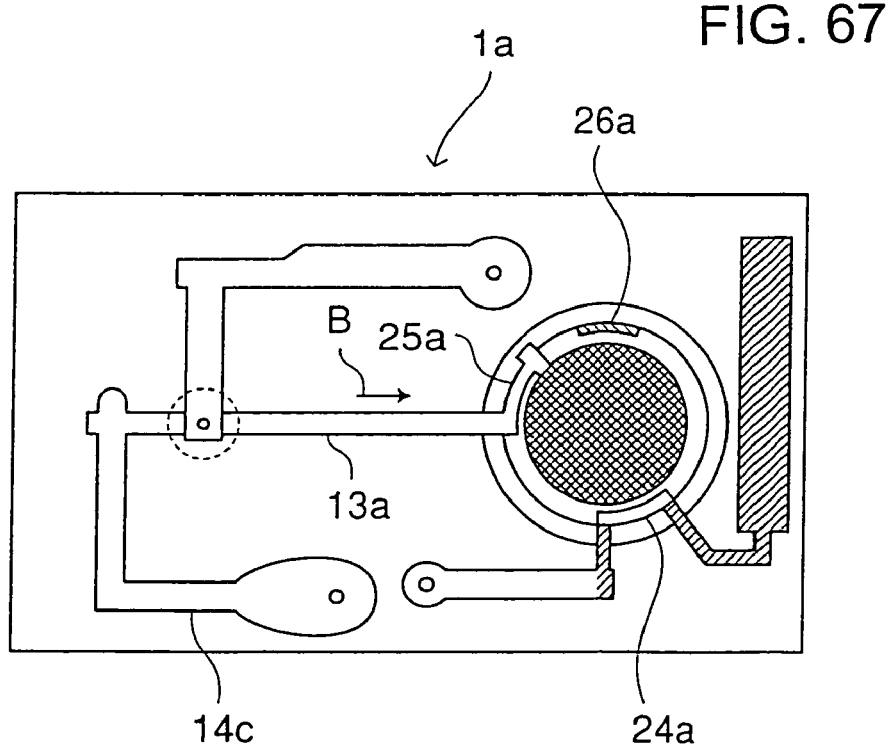

Subsequently, the syringe pump 103a repeats a T6-period sucking operation and a T7-period discharging operation N times, whereby the diluent and the sample flow back and forth between the channels 13a, 14c and the diluent container 5a in arrow directions A, B as shown in FIG. 66 (Steps S23 to S29). Thus, the diluent and the sample are sufficiently mixed and agitated for preparation of a 500-time diluted sample. The diluted sample is retained in the diluent container 5a as shown in FIG. 67.

Figure 68:
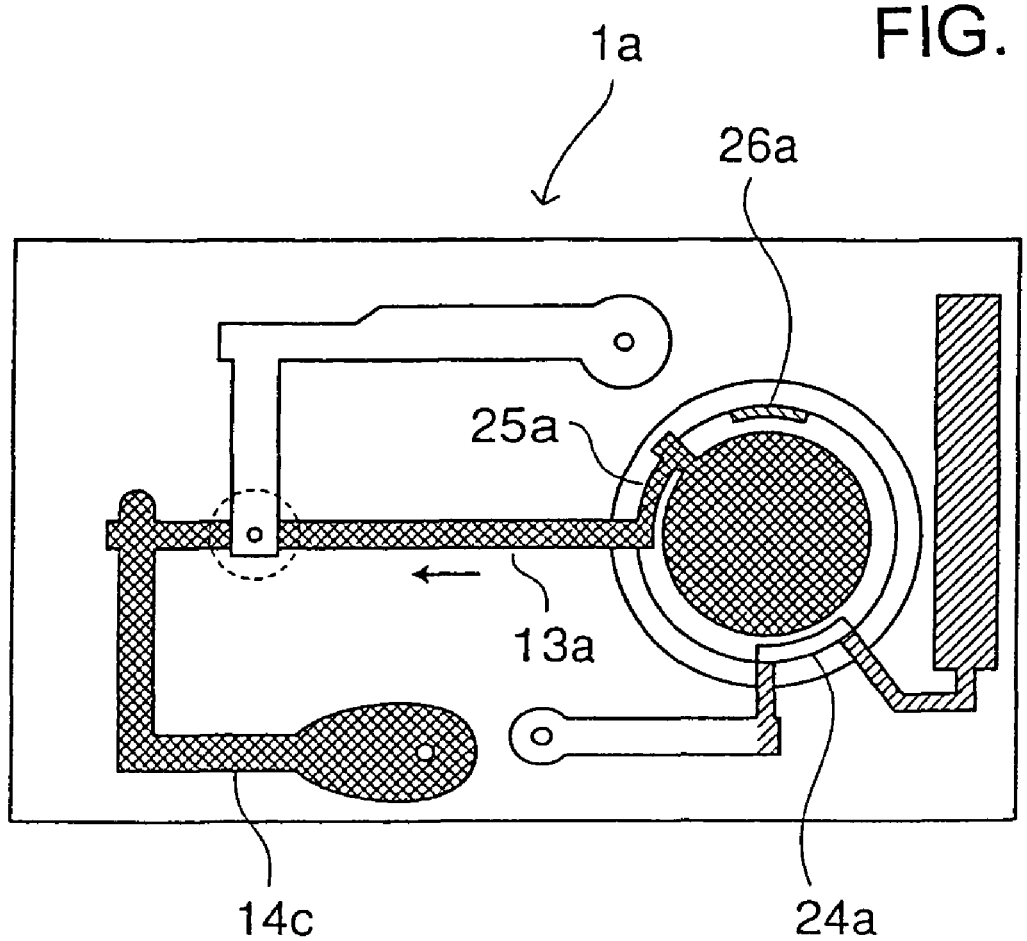

Then, the syringe pump 103a performs the sucking operation for a time period T8 (Steps S30 to S32), whereby the diluted sample is introduced into the channels 13a, 14c from the diluent container 5a as shown in FIG. 68. In this state, the photodiode 126 receives light emitted from the light emitting diode 125, whereby the intensity of the light transmitted through the diluted sample is measured (Step S32a).

Figure 69:
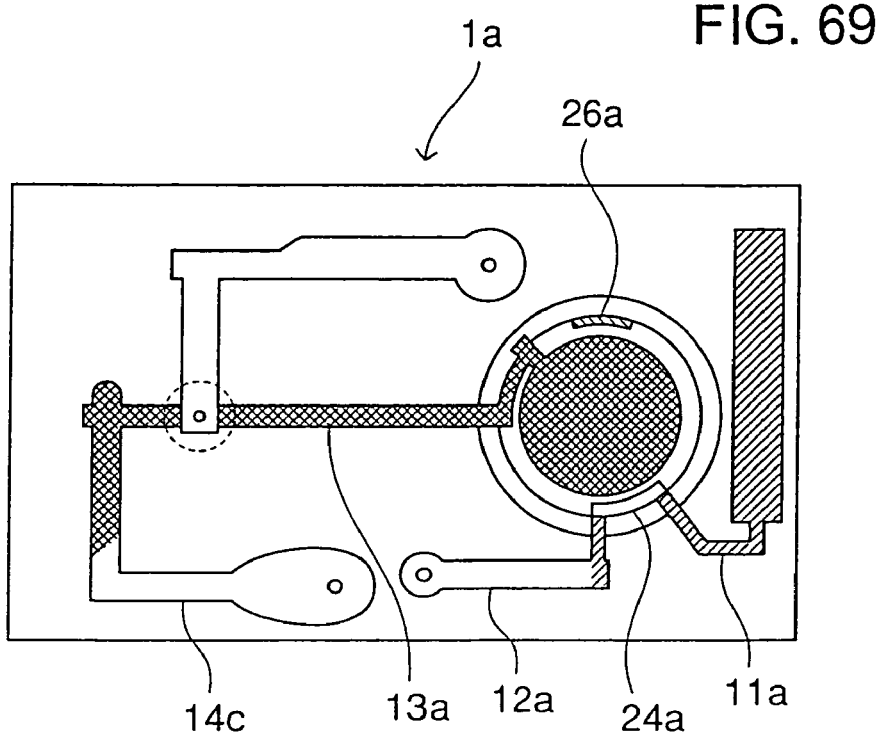

Subsequently, the syringe pump 103a performs the discharging operation for a time period T8a (Steps S32b to S32d), whereby the diluted sample is fed back into the diluent container 5a as shown in FIG. 69.

Figure 70:
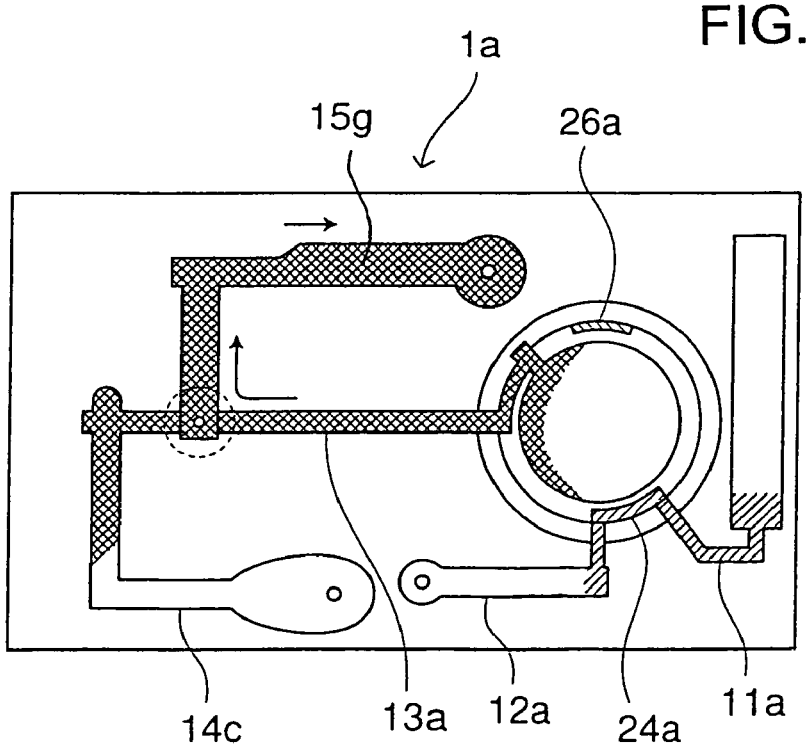

In turn, the syringe pump 104a performs a sucking operation for a time period T9, whereby the diluted sample flows toward the syringe pump 104a from the diluent container 5a via the pellet 33b and the channel 15g (i.e., via the measuring channel) as shown in FIG. 70. During this period, the signal processing section 106e measures an electrical resistance between the electrodes 34a and 35a (Steps S33 to S36).

Figure 71:
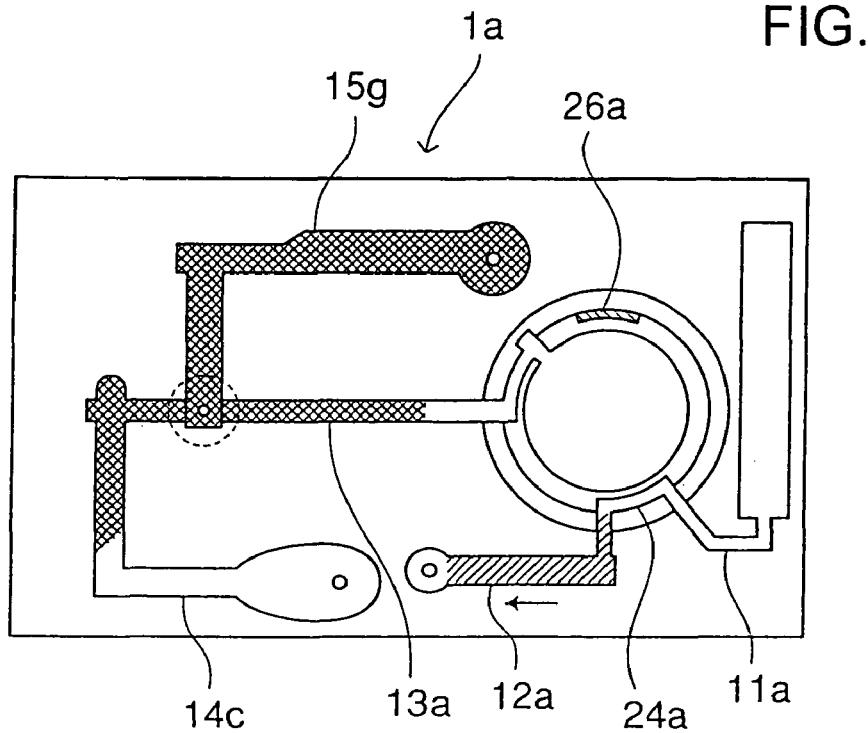

Then, the syringe pump 102a performs the sucking operation for a time period T10 (Steps S37 to S39), whereby all the sample remaining in the sample receiving section 4a is retained in the channel 12a as shown in FIG. 71. On the other hand, all the diluted sample in the diluent container 5a is retained in the channels 13a, 14c, 15g in Steps S33 to S36.

Figure 56A:
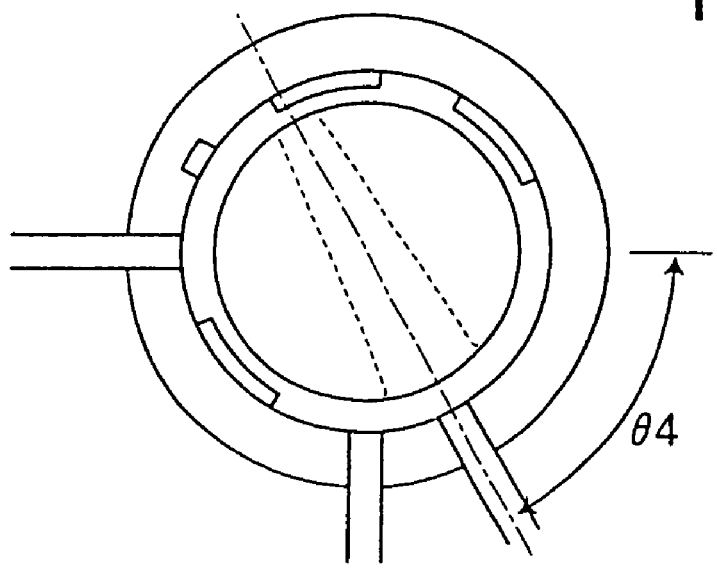
FIGS. 56(a) and 56(b) are diagrams for explaining the operation of the rotary valve of the measuring unit according to the second embodiment.
Figure 56B:
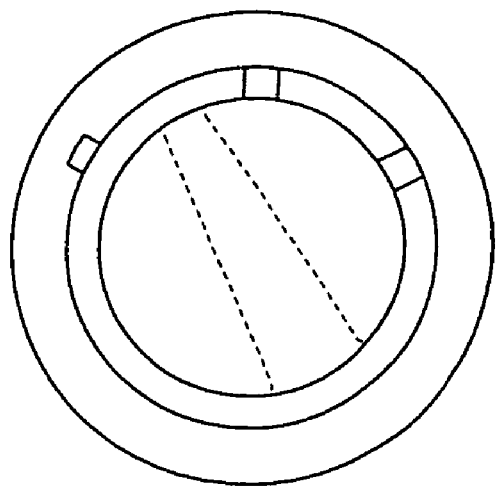
Figure 72:
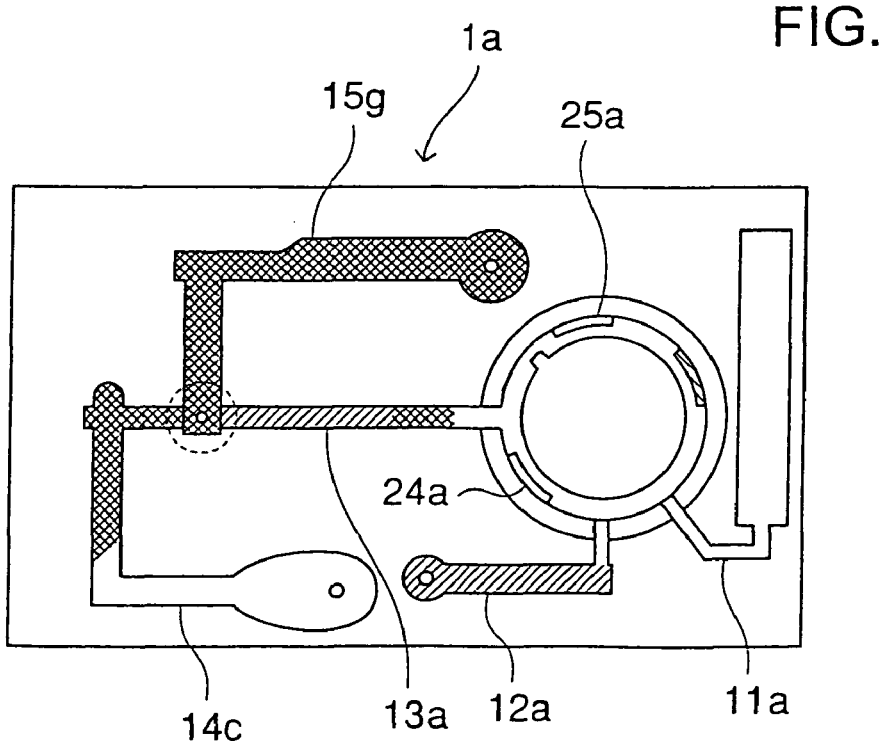

In turn, the stepping motor 105a is driven so that the inner cylinder 17a is rotated clockwise by an angle θ4 (Steps S40 to S42) thereby to reach a position as shown in FIGS. 56(a) and 56(b). Thus, the channel 11a is brought out of communication with the channel 12a as shown in FIG. 72.

In the aforesaid manner, the measuring operation is completed with the residual sample retained in the channel 12a and with the diluted sample retained in the channels 13a, 14c and 15g. After the through-hole 37a in the top wall of the rotary valve 6a is sealed again, the unit body 1a is removed from the analyzer 100a and discarded (Step S43).

7. Analysis of White Blood Cells and Hemoglobin

When the constant current from the constant direct current source 101a (FIG. 48) is applied to the diluted sample between the electrodes 34a and 35a in a space separated by the pellet 33b having the minute through-hole 33c as shown in FIG. 46, the electrical resistance between the electrodes 34a and 35a generally depends on the specific resistivity of a liquid component of the diluted sample. Particularly, the electrical resistance is determined by an electrical resistance of the liquid component present in and around the minute through-hole 33c, mainly depending on the diameter of the minute through-hole 33c and the thickness of the pellet 33b.

When a white blood cell passes through the minute through-hole 33c, the liquid component is removed by the volume of the white blood cell, so that the electrical resistance between the electrodes 34a and 35a changes. A change in the electrical resistance is detected as a voltage pulse generated between the electrodes 34a and 35a.

Therefore, the computing section 106d determines the number of white blood cells on the basis of the number of pulses. Since the amplitude of the pulse is proportional to the volume of the white blood cell, the computing section 106d detects the amplitude of each pulse, and calculates the spherical equivalent diameter of each white blood cell for preparation of a particle size distribution diagram.

Further, the computing section 106d determines the absorbance of the diluted sample by a known method on the basis of the transmitted light intensity of the diluent (blank level) and the transmitted light intensity of the diluted sample obtained by the optical characteristic measuring section 7b (FIG. 74). The amount of the hemoglobin is calculated on the basis of the absorbance thus determined.

In accordance with the present invention, the measuring unit is capable of quantifying a given sample therein without taking out the sample, so that the sample can be analyzed accurately and sanitarily.

What is claimed is:

1. A disposable measuring unit used in an analyzer for counting particles in a plurality of blood samples, comprising:
    a first plate being composed of a transparent resin;
    a second plate being combined with the first plate and composed of a transparent resin;
    a quantifying section for quantifying a blood sample in volume;
    a diluent agent for diluting the quantified sample;
    a diluent container for containing the diluent agent;
    a first pressure introduction port for introducing a pressure to mix the quantified sample and the diluent agent so as to prepare the diluted sample;
    a measuring section comprising an electrical characteristic measuring section for counting particles in the diluted sample, the electrical characteristic measuring section comprising a channel for passage of the diluted sample and two electrodes exposed to the channel, and
    a second pressure introduction port for introducing a pressure to transport the diluted sample to the measuring section,
    wherein the diluent container, the channel, the first pressure introduction port and the second pressure introduction port are formed by the first and second plates,
    wherein the disposable measuring unit is detachably connectable to an analyzer, and the pressure being supplied to the first and second pressure introduction ports by the analyzer,
    wherein the pressure is supplied to the first and second pressure introduction ports by the analyzer,
    wherein the disposable measuring unit is removed from the analyzer and is discarded with respect to each blood sample.

2. A disposable measuring unit as set forth in claim 1, further comprising a sample receiving section for receiving the blood sample to be quantified, the sample receiving section communicating with the quantifying section.

3. A disposable measuring unit as set forth in claim 2, wherein the sample receiving section is configured so as to receive a capillary blood sampler inserted therein.

4. A disposable measuring unit as set forth in claim 1, wherein the electrical characteristic measuring section a separation member having a small through-hole for passage of the diluted sample and provided in the channel.

5. A disposable measuring unit as set forth in claim 4, wherein the analyzer comprises an electric source, wherein the electrodes are exposed out of the measuring unit and electrically connected to the electric source when the measuring unit is connected to the analyzer.

6. A disposable measuring unit as set forth in claim 1, further comprising an optical characteristic measuring section for measuring an optical characteristic, the analyzer comprising a light source and a light receiving device, and the optical characteristic measuring section being pervious to light and configured so as to be interposed between the light source and the light receiving device when the measuring unit is connected to the analyzer.

7. A disposable measuring unit as set forth in claim 1, further comprising a first plate and a second plate combined with the first plate, wherein the quantifying section and the measuring section are provided in at least one of the first and second plates.

8. A disposable measuring unit as set forth in claim 7, wherein the first plate and a second plate are composed of a resin containing an antistatic agent.

9. A disposable measuring unit as set forth in claim 1, further comprising a space connected to the quantifying section for retaining a residual sample.

10. A disposable measuring unit as set forth in claim 1, further comprising a space for retaining the diluted sample after being measured by the measuring section.

11. A disposable measuring unit as set forth in claim 1, wherein the analyzer comprises a first pressure supplier for supplying the pressure and a second pressure supplier for supplying the pressure, wherein the first pressure introduction port is connected to the first pressure supplier and the second pressure introducing port is connected to the second pressure supplier when the measuring unit is connected to the analyzer.

12. A disposable measuring unit as set forth in claim 1, wherein the electrical characteristic measuring section counts particles selected from the group consisting of red blood cells, white blood cells and platelets.

13. A disposable measuring unit as set forth in claim 1, wherein the diluent container contains the diluent agent and a hemolyzing agent, the electrical characteristic measuring section counting white blood cells in the diluted and hemolyzed sample.

14. A disposable measuring unit as set forth in claim 13, wherein the measuring unit is measuring unit for counting the white blood cells and preparing a particle size distribution of the white blood cells.

15. A disposable measuring unit as set forth in claim 13, further comprising a channel for passage of the diluted sample and a bubble trapping portion in the channel for trapping a bubble in the diluted sample between the measuring section and the quantifying section.

16. A disposable measuring unit as set forth in claim 15, wherein the resin comprises a polycarbonate resin containing the antistatic agent or an acryl resin containing the antistatic agent.

17. A disposable measuring unit as set forth in claim 1, further comprising an optical characteristic measuring section for measuring an optical characteristic selected from the group consisting of the amount of hemoglobin, a blood coagulation period, the activity level of enzyme, the amount of billirubin and CRP.

18. A disposable measuring unit as set forth in claim 1, further comprising an optical characteristic measuring section for measuring an optical characteristic of the diluted and hemolyzed sample, wherein the measuring unit is measuring unit for counting white blood cells and measuring an amount of hemoglobin.

19. A disposable measuring unit used in an analyzer for counting particles in a plurality of blood samples, comprising, a first plate being composed of a transparent resin;

a second plate being combined with the first plate and composed of a transparent resin, and a pressure introduction port communicating with the main channel for introducing a pressure into the main channel to transport the sample from the quantifying section to the electrical resistance measuring section.

20. A disposable measuring unit as set forth in claim 19, wherein the electrical resistance measuring section comprises a main channel for transporting the sample therethrough, a separation plate having a small through-hole and provided in the main channel to obstruct the main channel, and two electrodes exposed to the main channel on opposite sides of the separation plate, the two electrodes being detachably connected to the constant direct current source.

21. A disposable measuring unit as set forth in claim 20, wherein the channel has a rectifying portion for rectifying the transported sample.

22. A disposable measuring unit as set forth in claim 19, wherein the electrical resistance measuring section has a space for retaining the measured sample.

23. A disposable measuring unit set forth in claim 19 further comprising:

a quantifying section for quantifying the sample in volume;

a main channel communicating between the quantifying section and the electrical resistance measuring section; and an electrical resistance measuring section for measuring electrical resistances of the particles in the blood sample, the electrical resistance measuring section comprising a channel for passage of the blood sample, wherein the channel is formed by the first and second plate, wherein the disposable measuring unit is detachably connected to an analyzer having a constant direct current source for supplying a direct current to the electrical resistance measuring section and a signal processing section for counting particles in the blood sample on the basis of the electrical resistances measured by the electrical resistance measuring section, wherein the disposable measuring unit is removed from the analyzer and is discarded with respect to each blood sample.

* * * * *